US011897969B2

(12) United States Patent
Tsimikas et al.

(10) Patent No.: US 11,897,969 B2
(45) Date of Patent: Feb. 13, 2024

(54) INHIBITION OF OXIDATION-SPECIFIC EPITOPES TO TREAT ISCHEMIC REPERFUSION INJURY

(71) Applicant: The Regents of the University of California, Oakland, CA (US)

(72) Inventors: Sotirios Tsimikas, San Diego, CA (US); Joseph L. Witztum, San Diego, CA (US); Xuchu Que, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/759,331

(22) PCT Filed: Oct. 26, 2018

(86) PCT No.: PCT/US2018/057793
§ 371 (c)(1),
(2) Date: Apr. 25, 2020

(87) PCT Pub. No.: WO2019/084460
PCT Pub. Date: May 2, 2019

(65) Prior Publication Data
US 2021/0221916 A1 Jul. 22, 2021

Related U.S. Application Data

(60) Provisional application No. 62/577,543, filed on Oct. 26, 2017.

(51) Int. Cl.
| | | |
|---|---|---|
| *A61K 39/395* | (2006.01) | |
| *A61P 9/10* | (2006.01) | |
| *C07K 16/44* | (2006.01) | |
| *A61P 9/00* | (2006.01) | |
| *A61K 9/00* | (2006.01) | |
| *A61K 45/06* | (2006.01) | |
| *A61K 39/00* | (2006.01) | |

(52) U.S. Cl.
CPC ............ *C07K 16/44* (2013.01); *A61K 9/0019* (2013.01); *A61K 39/39583* (2013.01); *A61K 45/06* (2013.01); *A61P 9/00* (2018.01); *A61P 9/10* (2018.01); *A61K 2039/505* (2013.01); *A61K 2039/54* (2013.01); *A61K 2039/545* (2013.01); *C07K 2317/565* (2013.01); *C07K 2317/622* (2013.01); *C07K 2317/76* (2013.01); *C07K 2317/92* (2013.01)

(58) Field of Classification Search
CPC ........ C07K 16/44; A61K 39/3589; A61P 9/10
See application file for complete search history.

(56) References Cited

U.S. PATENT DOCUMENTS

| | | |
|---|---|---|
| 6,271,199 B2 | 8/2001 | Brand et al. |
| 2012/0141466 A9 | 6/2012 | Heffernan et al. |
| 2012/0189631 A1 | 6/2012 | Shimohata et al. |
| 2015/0376268 A1 | 12/2015 | Witztum et al. |

FOREIGN PATENT DOCUMENTS

| | | |
|---|---|---|
| WO | 2007/026972 A2 | 3/2007 |
| WO | 2009/019260 A2 | 2/2009 |
| WO | 2014/113510 A1 | 7/2014 |
| WO | 2014/131034 A2 | 8/2014 |

OTHER PUBLICATIONS

Hausenloy et al, 2013 (Journal of Clinical Investigation. 123(1): 92-100).*
Wei et al, 2016. Acta Cardiol Sin. 32: 39-48.*
Fruhwirth et al, 2007. Biochimica et Biophysica Acta. 1772: 718-736.*
Kumar et al, 2009. Mayo Clin Proc. 84(10): 917-938.*
Verma et al, 2002. Circulation. 105: 2332-2336.*
Sousa et al (2012. Portuguese Journal of Cardiology. 31(10): 641-646).*
Binder, Christoph J. et al., "Innate sensing of oxidation-specific epitopes in health and disease", Nature Reviews Immunology, vol. 16, No. 8, Jun. 27, 2016, pp. 485-497.
Byun, Young Sup et al. "Oxidized Phospholipids on Apolipoprotein B-100 and Recurrent Ischemic Events Following Stroke or Transient Ischemic Attack", Journal of the American College of Cardiology, vol. 69, No. 2, Jan. 9, 2017, pp. 147-158.
Le Flao, Katell, Extended European Search Report, Application No. 18869918.5, European Patent Office, dated Aug. 30, 2021.
Tsimikas, Sotirios et al., "Oxidation-Specific Biomarkers, Prospective 15-Year Cardiovascular and Stroke Outcomes, and Net Reclassification of Cardiovascular Events", Journal of the American College of Cardiology, vol. 16, No. 21, Nov. 1, 2012, pp. 2218-2229.
Thomas, Shane, International Search Report and Written Opinion, PCT/US18/57793, United States Patent & Trademark Office, dated Mar. 7, 2019.
Lee, Sun Hwa, International Preliminary Report on Patentability and Written Opinion, PCT/US18/57793, The International Bureau of WIPO, May 7, 2020.
Matsuzaki et al., "Drug Delivery System, a Promising Therapeutic Strategy for Acute Myocardial Infarction", Drug Delivery System, Dec. 25, 2015, 30-4, pp. 276-285.
Sasaki, Daisuke, Office Action, Japan Patent Office, Application No. 2020-522288, dated Mar. 13, 2023.
Yamada, "[Series: knowledge of emergency required for internist; acute coronary syndrome: ACS]", Aug. 10, 2011, 100(8), pp. 2295-2301.

(Continued)

*Primary Examiner* — Zachary C Howard
(74) *Attorney, Agent, or Firm* — Gavrilovich, Dodd & Lindsey LLP

(57) ABSTRACT

The disclosure provides for methods and treatments of ischemic injury, reperfusion injury, stroke and myocardial infarctions by administering within minutes to hours an antibody or antibody fragment that bind to and inhibits the biological activity of OxPL in an affected tissue.

23 Claims, 9 Drawing Sheets
Specification includes a Sequence Listing.

(56) References Cited

OTHER PUBLICATIONS

Jaffe et al., "Prevention and Treatment of Microvascular Obstruction-Related Myocardial Injury and Coronary No-Reflow Following Percutaneous Coronary Intervention," J. Am. Coll. Cardiol. Intv., 3:695-704, 2010.

* cited by examiner

>E06scFv antibody fragment
(From 1 to 930. Translation 309 a.a. MW=33.65 kDa)

```
  1 ATGGAGACAGACACACTCCTGCTATGGGTACTGCTGCTCTGGGTTCCAGGTTCCACTGGTGACGCGGCCCAGCCG
  1  M   E   T   D   T   L   L   L   W   V   L   L   L   W   V   P   G   S   T   G   D   A   A   Q   P
 76 GCCAGGCGCGCCGTACGAAGCTTAGACATTGTGATGACTCAGTCTCCATCTTCCCTTTCTGTGTCAGCAGGTAAG
 26  A   R   R   A   V   R   S   L   D   I   V   M   T   Q   S   P   S   S   L   S   V   S   A   G   K
151 AAGGTCACCATTAGTTGCACGGCCAGTGAGAGCCTTTATTCAAGCAAACACAAGGTGCACTACTTGGCTTGGTAC
 51  K   V   T   I   S   C   T   A   S   E   S   L   Y   S   S   K   H   K   V   H   Y   L   A   W   Y
226 CAGAAGAAACCAGAGCAATCTCCTAAACTGCTGATATACGGGGCATCCAACCGATACATTGGGGTCCCTGATCGC
 76  Q   K   K   P   E   Q   S   P   K   L   L   I   Y   G   A   S   N   R   Y   I   G   V   P   D   R
301 TTCACAGGCAGTGGATCTGGGACAGATTTCACTCTGACCATCAGCAGTGTACAGGTTGAAGACCTCACACATTAT
101  F   T   G   S   G   S   G   T   D   F   T   L   T   I   S   S   V   Q   V   E   D   L   T   H   Y
376 TACTGTGCACAGTTTTACAGCTATCCGCTCACGTTCGGTGCTGGGACCAAGCTGGAAATCAAAGGTGGTGGAGGA
126  Y   C   A   Q   F   Y   S   Y   P   L   T   F   G   A   G   T   K   L   E   I   K   G   G   G   G
451 TCAGGTGGAGGTGGTTCAGGAGGTGGCGGATCCGAGGTGAAGCTGGTGGAGTCTGGAGGAGGCTTGGTACAGCCT
151  S   G   G   G   S   G   G   G   G   S   E   V   K   L   V   E   S   G   G   G   L   V   Q   P
526 GGGGGTTCTCTGAGACTCTCCTGTGCAACTTCTGGGTTCACCTTCAGTGATTTCTACATGGAGTGGGTCCGCCAG
176  G   G   S   L   R   L   S   C   A   T   S   G   F   T   F   S   D   F   Y   M   E   W   V   R   Q
601 GCTCCAGGGAAGAGACTGGAGTGGATTGCTGCAAGTAGAAACAAAGCTAATGATTATACAACAGAGTACGCTGAC
201  A   P   G   K   R   L   E   W   I   A   A   S   R   N   K   A   N   D   Y   T   T   E   Y   A   D
676 TCTGTGAAGGGTCGGTTCATCGTCTCCAGAGACACTTCCCAAAGCATCCTCTACCTTCAGATGAATGCCCTGAGA
226  S   V   K   G   R   F   I   V   S   R   D   T   S   Q   S   I   L   Y   L   Q   M   N   A   L   R
751 GCCGAGGACACTGCCATTTATTACTGTGCAAGAGATTACTACGGTAGTAGCTACTGGTACTTCGATGTCTGGGGC
251  A   E   D   T   A   I   Y   Y   C   A   R   D   Y   Y   G   S   S   Y   W   Y   F   D   V   W   G
826 GCAGGGACCACGGTCACCGTCTCCTCTCGAGGAGGGCCCGAACAAAAACTCATCTCAGAAGAGGATCTGAATAGC
276  A   G   T   T   V   T   V   S   S   R   G   G   P   E   Q   K   L   I   S   E   E   D   L   N   S
901 GCCGTCGACCATCATCATCATCATCATTGA
301  A   V   D   H   H   H   H   H   H   *
```

Annotation:
A.A. 1 ... 33 = Ig kappa chain leader sequence for antibody secretion.
A.A. 34 ... 146 = E06 light-chain variable region.
A.A. 42 ... 49 = FW1 region TFLAVTAS mutated to SSLSVSAG to enhance affinity to OxPL-PC/OxLDL and functional activity.
A.A. 57 ... 73 = "TASESLYSSKHKVHYLA" E06 L-chain CDR1.
A.A. 89 ... 95 = "GASNRYI" E06 L-chain CDR2.
A.A. 127 ... 136 = "CAQFYSYPLT" E06 L-chain CDR3.
A.A. 147 ... 161 = (Gly4Ser)x3 flexible linker peptides.
A.A. 162 ... 284 = E06 heavy-chain variable region with triple mutations of P201A, S224A and A225D to         increase antibody affinity to OxPL-PC/OxLDL.
A.A. 187 ... 193 = "GFTFSDF" E06 H-chain CDR1.
A.A. 213 ... 220 = "RNKANDYT" E06 H-chain CDR2.
A.A. 259 ... 274 = "CARDYYGSSYWYFDVW" E06 H-chain CDR3.
A.A. 289 ... 298 = myc epitope tag
A.A. 304 ... 309 = polyHis tag.

FIGURE 2

SEQUENCE LISTING

<160> NUMBER OF SEQ ID NOS: 14

<210> SEQ ID NO 1
<211> LENGTH: 930

```
<212> TYPE: DNA
<213> ORGANISM: Artificial Sequence
<220> FEATURE:
<223> OTHER INFORMATION: Engineered scFV E06 Antibody domain
<220> FEATURE:
<221> NAME/KEY: CDS
<222> LOCATION: (1)..(930)

<400> SEQUENCE: 1 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcc gta cga agc      96
Gly Ser Thr Gly Asp Ala Ala Gln Pro Ala Arg Arg Ala Val Arg Ser
            20                  25                  30 tta gac att gtg atg act cag tct cca tct tcc ctt tct gtg tca gca     144
Leu Asp Ile Val Met Thr Gln Ser Pro Ser Ser Leu Ser Val Ser Ala
        35                  40                  45 ggt aag aag gtc acc att agt tgc acg gcc agt gag agc ctt tat tca     192
Gly Lys Lys Val Thr Ile Ser Cys Thr Ala Ser Glu Ser Leu Tyr Ser
50                  55                  60 agc aaa cac aag gtg cac tac ttg gct tgg tac cag aag aaa cca gag     240
Ser Lys His Lys Val His Tyr Leu Ala Trp Tyr Gln Lys Lys Pro Glu
65                  70                  75                  80 caa tct cct aaa ctg ctg ata tac ggg gca tcc aac cga tac att ggg     288
Gln Ser Pro Lys Leu Leu Ile Tyr Gly Ala Ser Asn Arg Tyr Ile Gly
                85                  90                  95 gtc cct gat cgc ttc aca ggc agt gga tct ggg aca gat ttc act ctg     336
Val Pro Asp Arg Phe Thr Gly Ser Gly Ser Gly Thr Asp Phe Thr Leu
            100                 105                 110 acc atc agc agt gta cag gtt gaa gac ctc aca cat tat tac tgt gca     384
Thr Ile Ser Ser Val Gln Val Glu Asp Leu Thr His Tyr Tyr Cys Ala
        115                 120                 125 cag ttt tac agc tat ccg ctc acg ttc ggt gct ggg acc aag ctg gaa     432
Gln Phe Tyr Ser Tyr Pro Leu Thr Phe Gly Ala Gly Thr Lys Leu Glu
    130                 135                 140 atc aaa ggt ggt gga gga tca ggt gga ggt ggt tca gga ggt ggc gga     480
Ile Lys Gly Gly Gly Gly Ser Gly Gly Gly Gly Ser Gly Gly Gly Gly
145                 150                 155                 160 tcc gag gtg aag ctg gtg gag tct gga gga ggc ttg gta cag cct ggg     528
Ser Glu Val Lys Leu Val Glu Ser Gly Gly Gly Leu Val Gln Pro Gly
                165                 170                 175 ggt tct ctg aga ctc tcc tgt gca act tct ggg ttc acc ttc agt gat     576
Gly Ser Leu Arg Leu Ser Cys Ala Thr Ser Gly Phe Thr Phe Ser Asp
            180                 185                 190 ttc tac atg gag tgg gtc cgc cag gct cca ggg aag aga ctg gag tgg     624
Phe Tyr Met Glu Trp Val Arg Gln Ala Pro Gly Lys Arg Leu Glu Trp
        195                 200                 205 att gct gca agt aga aac aaa gct aat gat tat aca aca gag tac gct     672
Ile Ala Ala Ser Arg Asn Lys Ala Asn Asp Tyr Thr Thr Glu Tyr Ala
    210                 215                 220 gac tct gtg aag ggt cgg ttc atc gtc tcc aga gac act tcc caa agc     720
Asp Ser Val Lys Gly Arg Phe Ile Val Ser Arg Asp Thr Ser Gln Ser
225                 230                 235                 240 atc ctc tac ctt cag atg aat gcc ctg aga gcc gag gac act gcc att     768
Ile Leu Tyr Leu Gln Met Asn Ala Leu Arg Ala Glu Asp Thr Ala Ile
                245                 250                 255 tat tac tgt gca aga gat tac tac ggt agt agc tac tgg tac ttc gat     816
Tyr Tyr Cys Ala Arg Asp Tyr Tyr Gly Ser Ser Tyr Trp Tyr Phe Asp
            260                 265                 270
```

| | | | | | | | | | | | | | | | | |
|---|---|---|---|---|---|---|---|---|---|---|---|---|---|---|---|---|
| gtc | tgg | ggc | gca | ggg | acc | acg | gtc | acc | gtc | tcc | tct | cga | gga | ggg | ccc | 864 |
| Val | Trp | Gly | Ala | Gly | Thr | Thr | Val | Thr | Val | Ser | Ser | Arg | Gly | Gly | Pro | |
| | | 275 | | | | 280 | | | | 285 | | | | | | |
| gaa | caa | aaa | ctc | atc | tca | gaa | gag | gat | ctg | aat | agc | gcc | gtc | gac | cat | 912 |
| Glu | Gln | Lys | Leu | Ile | Ser | Glu | Glu | Asp | Leu | Asn | Ser | Ala | Val | Asp | His | |
| | 290 | | | | | 295 | | | | 300 | | | | | | |
| cat | cat | cat | cat | cat | tga | | | | | | | | | | | 930 |
| His | His | His | His | His | | | | | | | | | | | | |
| 305 | | | | | | | | | | | | | | | | |

<210> SEQ ID NO 2
<211> LENGTH: 309
<212> TYPE: PRT
<213> ORGANISM: Artificial Sequence
<220> FEATURE:
<223> OTHER INFORMATION: Synthetic Construct

<400> SEQUENCE: 2

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Asp Ile Val Met Thr Gln Ser Pro Ser Ser Leu Ser Val Ser Ala
        35                  40                  45

Gly Lys Lys Val Thr Ile Ser Cys Thr Ala Ser Glu Ser Leu Tyr Ser
50                  55                  60

Ser Lys His Lys Val His Tyr Leu Ala Trp Tyr Gln Lys Lys Pro Glu
65                  70                  75                  80

Gln Ser Pro Lys Leu Leu Ile Tyr Gly Ala Ser Asn Arg Tyr Ile Gly
            85                  90                  95

Val Pro Asp Arg Phe Thr Gly Ser Gly Ser Gly Thr Asp Phe Thr Leu
        100                 105                 110

Thr Ile Ser Ser Val Gln Val Glu Asp Leu Thr His Tyr Tyr Cys Ala
    115                 120                 125

Gln Phe Tyr Ser Tyr Pro Leu Thr Phe Gly Ala Gly Thr Lys Leu Glu
130                 135                 140

Ile Lys Gly Gly Gly Gly Ser Gly Gly Gly Gly Ser Gly Gly Gly Gly
145                 150                 155                 160

Ser Glu Val Lys Leu Val Glu Ser Gly Gly Gly Leu Val Gln Pro Gly
                165                 170                 175

Gly Ser Leu Arg Leu Ser Cys Ala Thr Ser Gly Phe Thr Phe Ser Asp
            180                 185                 190

Phe Tyr Met Glu Trp Val Arg Gln Ala Pro Gly Lys Arg Leu Glu Trp
        195                 200                 205

Ile Ala Ala Ser Arg Asn Lys Ala Asn Asp Tyr Thr Thr Glu Tyr Ala
210                 215                 220

Asp Ser Val Lys Gly Arg Phe Ile Val Ser Arg Asp Thr Ser Gln Ser
225                 230                 235                 240

Ile Leu Tyr Leu Gln Met Asn Ala Leu Arg Ala Glu Asp Thr Ala Ile
                245                 250                 255

Tyr Tyr Cys Ala Arg Asp Tyr Tyr Gly Ser Ser Tyr Trp Tyr Phe Asp
            260                 265                 270

Val Trp Gly Ala Gly Thr Thr Val Thr Val Ser Ser Arg Gly Gly Pro
        275                 280                 285

Glu Gln Lys Leu Ile Ser Glu Glu Asp Leu Asn Ser Ala Val Asp His
    290                 295                 300

His His His His His
305

```
<210> SEQ ID NO 3
<211> LENGTH: 1554
<212> TYPE: DNA
<213> ORGANISM: Artificial Sequence
<220> FEATURE:
<223> OTHER INFORMATION: Humanized E06 single-chain antibody with
      IgG1-Fc (E06scFv-Fc)
<220> FEATURE:
<221> NAME/KEY: CDS
<222> LOCATION: (1)..(1554)

<400> SEQUENCE: 3
```

| | | | | | | | | | | | | | | | | |
|---|---|---|---|---|---|---|---|---|---|---|---|---|---|---|---|---|
| atg | gag | acc | gac | aca | ctg | ttg | ttg | tgg | gtg | ttg | ctg | ctc | tgg | gtg | cca | 48 |
| Met | Glu | Thr | Asp | Thr | Leu | Leu | Leu | Trp | Val | Leu | Leu | Leu | Trp | Val | Pro | |
| 1 | | | | 5 | | | | | 10 | | | | | 15 | | |
| gga | agc | aca | ggt | gac | gct | gct | gac | atc | gtc | atg | acc | cag | agc | ccc | gac | 96 |
| Gly | Ser | Thr | Gly | Asp | Ala | Ala | Asp | Ile | Val | Met | Thr | Gln | Ser | Pro | Asp | |
| | | | 20 | | | | | 25 | | | | | 30 | | | |
| tct | ctc | gcg | gtt | tct | ctg | gga | gag | cgg | gca | aca | atc | aac | tgc | aca | gca | 144 |
| Ser | Leu | Ala | Val | Ser | Leu | Gly | Glu | Arg | Ala | Thr | Ile | Asn | Cys | Thr | Ala | |
| | | 35 | | | | | 40 | | | | | 45 | | | | |
| agc | gaa | tcc | ctg | tac | tca | tcc | aag | cac | gtg | cat | tac | ctc | gct | tgg | tac | 192 |
| Ser | Glu | Ser | Leu | Tyr | Ser | Ser | Lys | His | Val | His | Tyr | Leu | Ala | Trp | Tyr | |
| | 50 | | | | | 55 | | | | | 60 | | | | | |
| cag | cag | aaa | cca | ggg | caa | cca | cca | aag | ctc | ctc | att | tat | ggg | gcc | agc | 240 |
| Gln | Gln | Lys | Pro | Gly | Gln | Pro | Pro | Lys | Leu | Leu | Ile | Tyr | Gly | Ala | Ser | |
| 65 | | | | | 70 | | | | | 75 | | | | | 80 | |
| aac | aga | tat | att | gga | gtc | cca | gat | cga | ttc | agc | ggt | tcc | ggc | tcc | gga | 288 |
| Asn | Arg | Tyr | Ile | Gly | Val | Pro | Asp | Arg | Phe | Ser | Gly | Ser | Gly | Ser | Gly | |
| | | | | 85 | | | | | 90 | | | | | 95 | | |
| aca | gac | ttt | acc | ctc | acg | ata | agc | agc | ctg | cag | gcg | gaa | gat | gtg | gcc | 336 |
| Thr | Asp | Phe | Thr | Leu | Thr | Ile | Ser | Ser | Leu | Gln | Ala | Glu | Asp | Val | Ala | |
| | | | 100 | | | | | 105 | | | | | 110 | | | |
| gtg | tat | tac | tgc | gca | caa | ttc | tac | agc | tat | cct | ctg | acc | ttc | gga | gga | 384 |
| Val | Tyr | Tyr | Cys | Ala | Gln | Phe | Tyr | Ser | Tyr | Pro | Leu | Thr | Phe | Gly | Gly | |
| | | 115 | | | | | 120 | | | | | 125 | | | | |
| gga | aca | aaa | gtg | gag | atc | aaa | ggc | gga | ggt | gga | tcc | gga | ggg | ggt | gga | 432 |
| Gly | Thr | Lys | Val | Glu | Ile | Lys | Gly | Gly | Gly | Gly | Ser | Gly | Gly | Gly | Gly | |
| | 130 | | | | | 135 | | | | | 140 | | | | | |
| tct | gga | ggt | ggc | ggt | agt | gaa | gtg | cag | ctg | gtg | gaa | agt | gga | ggc | ggc | 480 |
| Ser | Gly | Gly | Gly | Gly | Ser | Glu | Val | Gln | Leu | Val | Glu | Ser | Gly | Gly | Gly | |
| 145 | | | | | 150 | | | | | 155 | | | | | 160 | |
| ctg | gtg | caa | cca | ggt | ggc | tct | ctg | agg | ctg | tca | tgc | gct | gcc | tct | gga | 528 |
| Leu | Val | Gln | Pro | Gly | Gly | Ser | Leu | Arg | Leu | Ser | Cys | Ala | Ala | Ser | Gly | |
| | | | | 165 | | | | | 170 | | | | | 175 | | |
| ttt | acc | ttc | tca | gat | ttc | tac | atg | gaa | tgg | gtc | aga | caa | gcc | cct | gga | 576 |
| Phe | Thr | Phe | Ser | Asp | Phe | Tyr | Met | Glu | Trp | Val | Arg | Gln | Ala | Pro | Gly | |
| | | | 180 | | | | | 185 | | | | | 190 | | | |
| aag | ggg | ctc | gag | tgg | gtg | gcc | gct | tcc | agg | aac | aag | gct | aat | gac | tac | 624 |
| Lys | Gly | Leu | Glu | Trp | Val | Ala | Ala | Ser | Arg | Asn | Lys | Ala | Asn | Asp | Tyr | |
| | | 195 | | | | | 200 | | | | | 205 | | | | |
| acc | aca | gag | tac | gcc | gca | agt | gtt | aaa | ggc | cgc | ttt | ata | atc | tcc | cgc | 672 |
| Thr | Thr | Glu | Tyr | Ala | Ala | Ser | Val | Lys | Gly | Arg | Phe | Ile | Ile | Ser | Arg | |
| | 210 | | | | | 215 | | | | | 220 | | | | | |
| gat | gac | tct | aag | aac | tcc | ttg | tac | ctt | caa | atg | aat | agt | ctc | aag | aca | 720 |
| Asp | Asp | Ser | Lys | Asn | Ser | Leu | Tyr | Leu | Gln | Met | Asn | Ser | Leu | Lys | Thr | |
| 225 | | | | | 230 | | | | | 235 | | | | | 240 | |

```
gaa gat aca gcg gta tac tac tgc gcc cgc gac tac tac gga tca agt         768
Glu Asp Thr Ala Val Tyr Tyr Cys Ala Arg Asp Tyr Tyr Gly Ser Ser
                245                 250                 255 tat tgg tac ttc gat gtt tgg aga gct ggc aca ctt gtg act gtc agc         816
Tyr Trp Tyr Phe Asp Val Trp Arg Ala Gly Thr Leu Val Thr Val Ser
            260                 265                 270 agt ctt gat cct aaa tcc tct gac aag acc tat acc tgc cca cct tgt         864
Ser Leu Asp Pro Lys Ser Ser Asp Lys Thr Tyr Thr Cys Pro Pro Cys
        275                 280                 285 ccc gcc cca gaa ctt ctg ggt ggc cca tcc gtg ttt ctg ttc cca cca         912
Pro Ala Pro Glu Leu Leu Gly Gly Pro Ser Val Phe Leu Phe Pro Pro
    290                 295                 300 aag cca aag gat aca ctc atg atc tct cgc act ccg gaa gtc acg tgc         960
Lys Pro Lys Asp Thr Leu Met Ile Ser Arg Thr Pro Glu Val Thr Cys
305                 310                 315                 320 gtc gtg gtt gat gtg tca cac gag gac ccg gag gtc aaa ttc aat tgg        1008
Val Val Val Asp Val Ser His Glu Asp Pro Glu Val Lys Phe Asn Trp
                325                 330                 335 tac gtg gac gga gtc gag gtg cac aac gcc aag aca aag cca cgc gaa        1056
Tyr Val Asp Gly Val Glu Val His Asn Ala Lys Thr Lys Pro Arg Glu
            340                 345                 350 gag cag tac aac agc acg tat aga gta gtg agc gtg ctg aca gtg ctc        1104
Glu Gln Tyr Asn Ser Thr Tyr Arg Val Val Ser Val Leu Thr Val Leu
        355                 360                 365 cac cag gat tgg ctt aac ggt aag gaa tac aag tgt aag gtc tcc aac        1152
His Gln Asp Trp Leu Asn Gly Lys Glu Tyr Lys Cys Lys Val Ser Asn
    370                 375                 380 aaa gct ctt cct gct cca ata gaa aag acc att tca aag gcc aag ggg        1200
Lys Ala Leu Pro Ala Pro Ile Glu Lys Thr Ile Ser Lys Ala Lys Gly
385                 390                 395                 400 caa cct cga gaa ccc cag gtg tac acg ctg cct ccc agc cga gag gag        1248
Gln Pro Arg Glu Pro Gln Val Tyr Thr Leu Pro Pro Ser Arg Glu Glu
                405                 410                 415 atg acc aag aac caa gta agt ctg aca tgc ctt gtc aaa ggg ttc tac        1296
Met Thr Lys Asn Gln Val Ser Leu Thr Cys Leu Val Lys Gly Phe Tyr
            420                 425                 430 ccc tca gac atc gcc gtg gaa tgg gaa agc aac ggt caa ccc gaa aac        1344
Pro Ser Asp Ile Ala Val Glu Trp Glu Ser Asn Gly Gln Pro Glu Asn
        435                 440                 445 aat tac aag aca acg ccg ccg gta ctc gat tcc gat ggt tcc ttt ttt        1392
Asn Tyr Lys Thr Thr Pro Pro Val Leu Asp Ser Asp Gly Ser Phe Phe
    450                 455                 460 ctg tac tcc aaa ctc acg gtg gac aag agt cga tgg cag cag gga aac        1440
Leu Tyr Ser Lys Leu Thr Val Asp Lys Ser Arg Trp Gln Gln Gly Asn
465                 470                 475                 480 gtt ttc tcc tgt tcc gtg atg cac gaa gca ctg cac aat cac tat acc        1488
Val Phe Ser Cys Ser Val Met His Glu Ala Leu His Asn His Tyr Thr
                485                 490                 495 cag aag tca ctg agt ttg agc cct ggc aaa gga ggg ggc gga tca cat        1536
Gln Lys Ser Leu Ser Leu Ser Pro Gly Lys Gly Gly Gly Gly Ser His
            500                 505                 510 cat cac cat cac cat taa                                                 1554
His His His His His
        515

<210> SEQ ID NO 4
<211> LENGTH: 517
<212> TYPE: PRT
<213> ORGANISM: Artificial Sequence
<220> FEATURE:
```

<223> OTHER INFORMATION: Synthetic Construct

<400> SEQUENCE: 4

```
Met Glu Thr Asp Thr Leu Leu Leu Trp Val Leu Leu Leu Trp Val Pro
1               5                   10                  15

Gly Ser Thr Gly Asp Ala Ala Asp Ile Val Met Thr Gln Ser Pro Asp
            20                  25                  30

Ser Leu Ala Val Ser Leu Gly Glu Arg Ala Thr Ile Asn Cys Thr Ala
        35                  40                  45

Ser Glu Ser Leu Tyr Ser Ser Lys His Val His Tyr Leu Ala Trp Tyr
    50                  55                  60

Gln Gln Lys Pro Gly Gln Pro Pro Lys Leu Leu Ile Tyr Gly Ala Ser
65                  70                  75                  80

Asn Arg Tyr Ile Gly Val Pro Asp Arg Phe Ser Gly Ser Gly Ser Gly
                85                  90                  95

Thr Asp Phe Thr Leu Thr Ile Ser Ser Leu Gln Ala Glu Asp Val Ala
            100                 105                 110

Val Tyr Tyr Cys Ala Gln Phe Tyr Ser Tyr Pro Leu Thr Phe Gly Gly
        115                 120                 125

Gly Thr Lys Val Glu Ile Lys Gly Gly Gly Gly Ser Gly Gly Gly Gly
    130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Ala Ala Ser Gly
                165                 170                 175

Phe Thr Phe Ser Asp Phe Tyr Met Glu Trp Val Arg Gln Ala Pro Gly
            180                 185                 190

Lys Gly Leu Glu Trp Val Ala Ala Ser Arg Asn Lys Ala Asn Asp Tyr
        195                 200                 205

Thr Thr Glu Tyr Ala Ala Ser Val Lys Gly Arg Phe Ile Ile Ser Arg
    210                 215                 220

Asp Asp Ser Lys Asn Ser Leu Tyr Leu Gln Met Asn Ser Leu Lys Thr
225                 230                 235                 240

Glu Asp Thr Ala Val Tyr Tyr Cys Ala Arg Asp Tyr Tyr Gly Ser Ser
                245                 250                 255

Tyr Trp Tyr Phe Asp Val Trp Arg Ala Gly Thr Leu Val Thr Val Ser
            260                 265                 270

Ser Leu Asp Pro Lys Ser Ser Asp Lys Thr Tyr Thr Cys Pro Pro Cys
        275                 280                 285

Pro Ala Pro Glu Leu Leu Gly Gly Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
    370                 375                 380

Lys Ala Leu Pro Ala Pro Ile Glu Lys Thr Ile Ser Lys Ala Lys Gly
385                 390                 395                 400
```

```
Gln Pro Arg Glu Pro Gln Val Tyr Thr Leu Pro Pro Ser Arg Glu Glu
            405                 410                 415

Met Thr Lys Asn Gln Val Ser Leu Thr Cys Leu Val Lys Gly Phe Tyr
        420                 425                 430

Pro Ser Asp Ile Ala Val Glu Trp Glu Ser Asn Gly Gln Pro Glu Asn
            435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
            485                 490                 495

Gln Lys Ser Leu Ser Leu Ser Pro Gly Lys Gly Gly Gly Ser His
        500                 505                 510

His His His His His
        515

<210> SEQ ID NO 5
<211> LENGTH: 5
<212> TYPE: PRT
<213> ORGANISM: Artificial Sequence
<220> FEATURE:
<223> OTHER INFORMATION: Peptide Linker

<400> SEQUENCE: 5

Gly Gly Gly Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: VH CDR1

<400> SEQUENCE: 6

Gly Phe Thr Phe Ser Asp Phe
1               5

<210> SEQ ID NO 7
<211> LENGTH: 8
<212> TYPE: PRT
<213> ORGANISM: Artificial Sequence
<220> FEATURE:
<223> OTHER INFORMATION: VH CDR2

<400> SEQUENCE: 7

Arg Asn Lys Ala Asn Asp Tyr Thr
1               5

<210> SEQ ID NO 8
<211> LENGTH: 16
<212> TYPE: PRT
<213> ORGANISM: Artificial Sequence
<220> FEATURE:
<223> OTHER INFORMATION: VH CDR3

<400> SEQUENCE: 8

Cys Ala Arg Asp Tyr Tyr Gly Ser Ser Tyr Trp Tyr Phe Asp Val Trp
1               5                   10                  15

<210> SEQ ID NO 9
<211> LENGTH: 17
```

```
<212> TYPE: PRT
<213> ORGANISM: Artificial Sequence
<220> FEATURE:
<223> OTHER INFORMATION: VL CDR1

<400> SEQUENCE: 9

Thr Ala Ser Glu Ser Leu Tyr Ser Ser Lys His Lys Val His Tyr Leu
1               5                   10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: VL CDR2

<400> SEQUENCE: 10

Gly Ala Ser Asn Arg Tyr Ile
1               5

<210> SEQ ID NO 11
<211> LENGTH: 10
<212> TYPE: PRT
<213> ORGANISM: Artificial Sequence
<220> FEATURE:
<223> OTHER INFORMATION: VL CDR3

<400> SEQUENCE: 11

Cys Ala Gln Phe Tyr Ser Tyr Pro Leu Thr
1               5                   10

<210> SEQ ID NO 12
<211> LENGTH: 16
<212> TYPE: PRT
<213> ORGANISM: Artificial Sequence
<220> FEATURE:
<223> OTHER INFORMATION: VL CDR1-humanized

<400> SEQUENCE: 12

Thr Ala Ser Glu Ser Leu Tyr Ser Ser Lys His Val His Tyr Leu Ala
1               5                   10                  15

<210> SEQ ID NO 13
<211> LENGTH: 1587
<212> TYPE: DNA
<213> ORGANISM: Artificial Sequence
<220> FEATURE:
<223> OTHER INFORMATION: Chimeric E06scFv-human IgG1-Fc antibody
      sequence
<220> FEATURE:
<221> NAME/KEY: CDS
<222> LOCATION: (1)..(1587)

<400> SEQUENCE: 13 atg gag aca gac aca ctc ctg cta tgg gta ctg ctg ctc tgg gtt cca        48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcc gta cga agc        96
Gly Ser Thr Gly Asp Ala Ala Gln Pro Ala Arg Arg Ala Val Arg Ser
                20                  25                  30 tta gac att gtg atg act cag tct cca tct tcc ctt tct gtg tca gca       144
Leu Asp Ile Val Met Thr Gln Ser Pro Ser Ser Leu Ser Val Ser Ala
            35                  40                  45
```

-continued

| | | |
|---|---|---|
| ggt aag aag gtc acc att agt tgc acg gcc agt gag agc ctt tat tca<br>Gly Lys Lys Val Thr Ile Ser Cys Thr Ala Ser Glu Ser Leu Tyr Ser<br>50                        55                       60 | 192 |
| agc aaa cac aag gtg cac tac ttg gct tgg tac cag aag aaa cca gag<br>Ser Lys His Lys Val His Tyr Leu Ala Trp Tyr Gln Lys Lys Pro Glu<br>65                  70                      75                 80 | 240 |
| caa tct cct aaa ctg ctg ata tac ggg gca tcc aac cga tac att ggg<br>Gln Ser Pro Lys Leu Leu Ile Tyr Gly Ala Ser Asn Arg Tyr Ile Gly<br>                    85                      90                      95 | 288 |
| gtc cct gat cgc ttc aca ggc agt gga tct ggg aca gat ttc act ctg<br>Val Pro Asp Arg Phe Thr Gly Ser Gly Ser Gly Thr Asp Phe Thr Leu<br>            100                     105                    110 | 336 |
| acc atc agc agt gta cag gtt gaa gac ctc aca cat tat tac tgt gca<br>Thr Ile Ser Ser Val Gln Val Glu Asp Leu Thr His Tyr Tyr Cys Ala<br>               115                     120                    125 | 384 |
| cag ttt tac agc tat ccg ctc acg ttc ggt gct ggg acc aag ctg gaa<br>Gln Phe Tyr Ser Tyr Pro Leu Thr Phe Gly Ala Gly Thr Lys Leu Glu<br>            130                     135                    140 | 432 |
| atc aaa ggt ggt gga gga tca ggt gga ggt ggt tca gga ggt ggc gga<br>Ile Lys Gly Gly Gly Gly Ser Gly Gly Gly Gly Ser Gly Gly Gly Gly<br>145                       150                     155                    160 | 480 |
| tcc gag gtg aag ctg gtg gag tct gga gga ggc ttg gta cag cct ggg<br>Ser Glu Val Lys Leu Val Glu Ser Gly Gly Gly Leu Val Gln Pro Gly<br>               165                     170                    175 | 528 |
| ggt tct ctg aga ctc tcc tgt gca act tct ggg ttc acc ttc agt gat<br>Gly Ser Leu Arg Leu Ser Cys Ala Thr Ser Gly Phe Thr Phe Ser Asp<br>            180                     185                    190 | 576 |
| ttc tac atg gag tgg gtc cgc cag gct cca ggg aag aga ctg gag tgg<br>Phe Tyr Met Glu Trp Val Arg Gln Ala Pro Gly Lys Arg Leu Glu Trp<br>               195                     200                    205 | 624 |
| att gct gca agt aga aac aaa gct aat gat tat aca aca gag tac gct<br>Ile Ala Ala Ser Arg Asn Lys Ala Asn Asp Tyr Thr Thr Glu Tyr Ala<br>            210                     215                    220 | 672 |
| gac tct gtg aag ggt cgg ttc atc gtc tcc aga gac act tcc caa agc<br>Asp Ser Val Lys Gly Arg Phe Ile Val Ser Arg Asp Thr Ser Gln Ser<br>225                       230                     235                    240 | 720 |
| atc ctc tac ctt cag atg aat gcc ctg aga gcc gag gac act gcc att<br>Ile Leu Tyr Leu Gln Met Asn Ala Leu Arg Ala Glu Asp Thr Ala Ile<br>               245                     250                    255 | 768 |
| tat tac tgt gca aga gat tac tac ggt agt agc tac tgg tac ttc gat<br>Tyr Tyr Cys Ala Arg Asp Tyr Tyr Gly Ser Ser Tyr Trp Tyr Phe Asp<br>            260                     265                    270 | 816 |
| gtc tgg ggc gca ggg acc acg gtc acc gtc tcc tct ctg gac ccg aag<br>Val Trp Gly Ala Gly Thr Thr Val Thr Val Ser Ser Leu Asp Pro Lys<br>            275                     280                    285 | 864 |
| tct tct gac aaa act tac aca tgc cca ccg tgc cca gca cct gaa ctc<br>Ser Ser Asp Lys Thr Tyr Thr Cys Pro Pro Cys Pro Ala Pro Glu Leu<br>290                       295                     300 | 912 |
| ctg ggg gga ccg tca gtc ttc ctc ttc ccc cca aaa ccc aag gac acc<br>Leu Gly Gly Pro Ser Val Phe Leu Phe Pro Pro Lys Pro Lys Asp Thr<br>305                       310                     315                    320 | 960 |
| ctc atg atc tcc cgg acc cct gag gtc aca tgc gtg gtg gtg gac gtg<br>Leu Met Ile Ser Arg Thr Pro Glu Val Thr Cys Val Val Val Asp Val<br>               325                     330                    335 | 1008 |
| agc cac gaa gac cct gag gtc aag ttc aac tgg tac gtg gac ggc gtg<br>Ser His Glu Asp Pro Glu Val Lys Phe Asn Trp Tyr Val Asp Gly Val<br>            340                     345                    350 | 1056 |

```
gag gtg cat aat gcc aag aca aag ccg cgg gag gag cag tac aac agc        1104
Glu Val His Asn Ala Lys Thr Lys Pro Arg Glu Glu Gln Tyr Asn Ser
            355                 360                 365 acg tac cgt gtg gtc agc gtc ctc acc gtc ctg cac cag gac tgg ctg        1152
Thr Tyr Arg Val Val Ser Val Leu Thr Val Leu His Gln Asp Trp Leu
370                 375                 380 aat ggc aag gag tac aag tgc aag gtc tcc aac aaa gcc ctc cca gcc        1200
Asn Gly Lys Glu Tyr Lys Cys Lys Val Ser Asn Lys Ala Leu Pro Ala
385                 390                 395                 400 ccc atc gag aaa acc atc tcc aaa gcc aaa ggg cag ccc cga gaa cca        1248
Pro Ile Glu Lys Thr Ile Ser Lys Ala Lys Gly Gln Pro Arg Glu Pro
                405                 410                 415 cag gtg tac acc ctg ccc cca tcc cgg gag gag atg acc aag aac cag        1296
Gln Val Tyr Thr Leu Pro Pro Ser Arg Glu Glu Met Thr Lys Asn Gln
            420                 425                 430 gtc agc ctg acc tgc ctg gtc aaa ggc ttc tat ccc agc gac atc gcc        1344
Val Ser Leu Thr Cys Leu Val Lys Gly Phe Tyr Pro Ser Asp Ile Ala
        435                 440                 445 gtg gag tgg gag agc aat ggg cag ccg gag aac aac tac aag acc acg        1392
Val Glu Trp Glu Ser Asn Gly Gln Pro Glu Asn Asn Tyr Lys Thr Thr
    450                 455                 460 cct ccc gtg ctg gac tcc gac ggc tcc ttc ttc ctc tac agc aag ctc        1440
Pro Pro Val Leu Asp Ser Asp Gly Ser Phe Phe Leu Tyr Ser Lys Leu
465                 470                 475                 480 acc gtg gac aag agc agg tgg cag cag ggg aac gtc ttc tca tgc tcc        1488
Thr Val Asp Lys Ser Arg Trp Gln Gln Gly Asn Val Phe Ser Cys Ser
                485                 490                 495 gtg atg cac gag gct ctg cac aac cac tac acg cag aag agc ctc tcc        1536
Val Met His Glu Ala Leu His Asn His Tyr Thr Gln Lys Ser Leu Ser
            500                 505                 510 ctg tct ccg ggt aaa ggt gga ggt gga tca cat cat cat cat cat cat        1584
Leu Ser Pro Gly Lys Gly Gly Gly Gly Ser His His His His His His
        515                 520                 525 taa                                                                    1587

<210> SEQ ID NO 14
<211> LENGTH: 528
<212> TYPE: PRT
<213> ORGANISM: Artificial Sequence
<220> FEATURE:
<223> OTHER INFORMATION: Synthetic Construct

<400> SEQUENCE: 14

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Val Arg Ser
            20                  25                  30

Leu Asp Ile Val Met Thr Gln Ser Pro Ser Ser Leu Ser Val Ser Ala
        35                  40                  45

Gly Lys Lys Val Thr Ile Ser Cys Thr Ala Ser Glu Ser Leu Tyr Ser
    50                  55                  60

Ser Lys His Lys Val His Tyr Leu Ala Trp Tyr Gln Lys Lys Pro Glu
65                  70                  75                  80

Gln Ser Pro Lys Leu Leu Ile Tyr Gly Ala Ser Asn Arg Tyr Ile Gly
                85                  90                  95

Val Pro Asp Arg Phe Thr Gly Ser Gly Ser Gly Thr Asp Phe Thr Leu
            100                 105                 110
```

Thr Ile Ser Ser Val Gln Val Glu Asp Leu Thr His Tyr Tyr Cys Ala
            115                 120                 125

Gln Phe Tyr Ser Tyr Pro Leu Thr Phe Gly Ala Gly Thr Lys Leu Glu
        130                 135                 140

Ile Lys Gly Gly Gly Gly Ser Gly Gly Gly Gly Ser Gly Gly Gly Gly
145                 150                 155                 160

Ser Glu Val Lys Leu Val Glu Ser Gly Gly Leu Val Gln Pro Gly
                165                 170                 175

Gly Ser Leu Arg Leu Ser Cys Ala Thr Ser Gly Phe Thr Phe Ser Asp
            180                 185                 190

Phe Tyr Met Glu Trp Val Arg Gln Ala Pro Gly Lys Arg Leu Glu Trp
        195                 200                 205

Ile Ala Ala Ser Arg Asn Lys Ala Asn Asp Tyr Thr Thr Glu Tyr Ala
        210                 215                 220

Asp Ser Val Lys Gly Arg Phe Ile Val Ser Arg Asp Thr Ser Gln Ser
225                 230                 235                 240

Ile Leu Tyr Leu Gln Met Asn Ala Leu Arg Ala Glu Asp Thr Ala Ile
            245                 250                 255

Tyr Tyr Cys Ala Arg Asp Tyr Tyr Gly Ser Ser Tyr Trp Tyr Phe Asp
        260                 265                 270

Val Trp Gly Ala Gly Thr Thr Val Thr Val Ser Ser Leu Asp Pro Lys
        275                 280                 285

Ser Ser Asp Lys Thr Tyr Thr Cys Pro Pro Cys Pro Ala Pro Glu Leu
        290                 295                 300

Leu Gly Gly Pro Ser Val Phe Leu Phe Pro Pro Lys Pro Lys Asp Thr
305                 310                 315                 320

Leu Met Ile Ser Arg Thr Pro Glu Val Thr Cys Val Val Val Asp Val
            325                 330                 335

Ser His Glu Asp Pro Glu Val Lys Phe Asn Trp Tyr Val Asp Gly Val
        340                 345                 350

Glu Val His Asn Ala Lys Thr Lys Pro Arg Glu Glu Gln Tyr Asn Ser
        355                 360                 365

Thr Tyr Arg Val Val Ser Val Leu Thr Val Leu His Gln Asp Trp Leu
        370                 375                 380

Asn Gly Lys Glu Tyr Lys Cys Lys Val Ser Asn Lys Ala Leu Pro Ala
385                 390                 395                 400

Pro Ile Glu Lys Thr Ile Ser Lys Ala Lys Gly Gln Pro Arg Glu Pro
            405                 410                 415

Gln Val Tyr Thr Leu Pro Pro Ser Arg Glu Glu Met Thr Lys Asn Gln
        420                 425                 430

Val Ser Leu Thr Cys Leu Val Lys Gly Phe Tyr Pro Ser Asp Ile Ala
        435                 440                 445

Val Glu Trp Glu Ser Asn Gly Gln Pro Glu Asn Asn Tyr Lys Thr Thr
        450                 455                 460

Pro Pro Val Leu Asp Ser Asp Gly Ser Phe Phe Leu Tyr Ser Lys Leu
465                 470                 475                 480

Thr Val Asp Lys Ser Arg Trp Gln Gln Gly Asn Val Phe Ser Cys Ser
            485                 490                 495

Val Met His Glu Ala Leu His Asn His Tyr Thr Gln Lys Ser Leu Ser
        500                 505                 510

Leu Ser Pro Gly Lys Gly Gly Gly Gly Ser His His His His His His
        515                 520                 525

INHIBITION OF OXIDATION-SPECIFIC EPITOPES TO TREAT ISCHEMIC REPERFUSION INJURY

CROSS REFERENCE TO RELATED APPLICATIONS

This application is a U.S. National Phase Application filed under 35 U.S.C. § 371 and claims the benefit of International Application No. PCT/US2018/057793, filed Oct. 26, 2018, which application claims priority uder 35 U.S.C. § 119 from Provisional Application Ser. No. 62/577,543, filed Oct. 26, 2017, the disclosures of which are incorporated herein by reference.

STATEMENT REGARDING FEDERALLY SPONSORED RESEARCH

This invention was made with Government support under Grant Nos. HL086559, HL088093 and HL119828, awarded by the National Institutes of Health. The Government has certain rights in the invention.

TECHNICAL FIELD

The disclosure provides methods and compositions for treating thrombosis, myocardial infarction and/or ischemia and reperfusion injury. The method includes administering an antibody or antibody fragment, e.g., single chain variable region (scFv) that bind to oxidized phospholipids.

INCORPORATION BY REFERENCE OF SEQUENCE LISTING

Accompanying this filing is a Sequence Listing entitled "Sequence_ST25.txt", created on Oct. 26, 2018 and having 34,214 bytes of data, machine formatted on IBM-PC, MS-Windows operating system. The sequence listing is hereby incorporated herein by reference in its entirety for all purposes.

BACKGROUND

Coronary artery disease remains the leading cause of morbidity and mortality worldwide.

Major advances in the treatment of acute coronary syndromes and myocardial infarction (MI) have occurred over the past 20 years. In particular, the ability to rapidly restore blood flow to the myocardium during ischemia, using thrombolytic or percutaneous interventional approaches has resulted in improved outcomes. However, despite timely revascularization and contemporary medical therapies, one-quarter of patients presenting with an anterior ST elevation MI (STEMI) can experience death or heart failure. Restoration of blood flow to the culprit vessel can paradoxically induce cardiomyocyte death, a phenomenon termed reperfusion injury, which can account for up to 50% of the final infarct size and contribute to poor outcomes. Despite intense investigation, there have been multiple failures of pharmacologic attempts to reduce ischemia reperfusion (IR) injury. Currently, there are no effective pharmacologic therapies, and there is an urgent need to further understand this process.

SUMMARY

This disclosure describes the potential for improving organ function during episodes of ischemia reperfusion (I/R) injury. The process of reperfusion creates enhanced oxidative stress and generation of oxidation specific epitopes (OSE), which are products of lipid peroxidation reactions, and which can be oxidized lipids and/or oxidized lipids that have covalently bound to proteins via reactive groups. Prime examples of such OSE include phosphocholine containing oxidized phospholipids (OxPL) and or malondialdehyde (MDA). Both OxPL and MDA are known to directly initiate proinflammatory gene signaling, as does OxPL- and MDA-protein adducts. OxPL also potently induce apoptosis and cell death. The disclosure demonstrates that antibodies and antibody fragments that bind to OSE and OxPL can be used to inhibit I/R. Exemplary antibodies and antibody fragments useful in the disclosure include E06 and an antibody fragment (scFv) of the E06 antibody, termed E06-scFv. The E06-scFv binds to OxPL and thus inhibits their proinflammatory effects.

The disclosure provides a method of treating a subject at risk of having or having ischemic-reperfusion injury, comprising administering to a subject that is at risk of suffering or has suffered an ischemic event a therapeutically effective amount of an antibody or antibody fragment that specifically binds to oxidation-specific epitopes (OSEs). In one embodiment, the OSE is present on an oxidized phospholipid (OxPL). In another embodiment, the ischemic event is associated with a condition selected from the group consisting of cerebral ischemia; intestinal ischemia; spinal cord ischemia; cardiovascular ischemia; myocardial ischemia associated with myocardial infarction; myocardial ischemia associated with CHF, ischemia associated with age-related macular degeneration (AME); liver ischemia; kidney/renal ischemia; dermal ischemia; vasoconstriction-induced tissue ischemia; penile ischemia as a consequence of priapism and erectile dysfunction; ischemia associated with thromboembolytic disease; ischemia associated with microvascular disease; ischemia associated with thrombosis; and ischemia associated with diabetic ulcers, gangrenous conditions, post-trauma syndrome, cardiac arrest resuscitation, hypothermia, peripheral nerve damage and neuropathies. In still another embodiment, the ischemic event is the result of an induced injury. In a further embodiment, the induced injury is selected from surgery, transplantation, accidental trauma and mechanical support devices. In still a further embodiment, the surgery is selected from the group consisting of heart surgery, kidney surgery, brain surgery, liver surgery, and bypass surgery. In yet another embodiment, the antibody or antibody fragment lacks complement activation or inflammatory cell recruitment activity. In another embodiment, the antibody or antibody fragment has the same or substantially the same binding affinity as and E06 antibody. In yet another embodiment, the antibody or antibody fragment binds to a phosphocholine headgroup of an oxidized phospholipid. In still another embodiment, the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) selected from the group consisting of: SEQ ID NO:6 and sequence that are at least 95%, 96%, 97%, 98%, 99% or 99.9% identical to SEQ ID NO:6; SEQ ID NO:7 and sequence that are at least 95%, 96%, 97%, 98%, 99% or 99.9% identical to SEQ ID NO:7; and SEQ ID NO:8 and sequence that are at least 95%, 96%, 97%, 98%, 99% or 99.9% identical to SEQ ID NO:8; and (b) the $V_L$ domain comprises an amino acid sequence that includes one, two or three complementarity determining regions (CDRs) selected from the group consisting of: SEQ ID NO:9 or 12 and sequence that are at least 95%, 96%, 97%, 98%, 99% or 99.9% identical to SEQ ID NO:9 or 12; SEQ ID NO:10 and sequence that are at least 95%, 96%, 97%, 98%, 99% or 99.9% identical to SEQ ID NO:10; and SEQ ID NO:11 and sequence that are at least 95%, 96%, 97%, 98%, 99% or 99.9% identical to SEQ ID NO:11 in an amount effective to reduce ischemic injury and/or tissue damage. In yet another or further embodiment, the disease associated with thrombosis is sickle cell disease, deep vein thrombosis, pulmonary embolism, cardiac embolism, hypercoagulable state, thrombophilia, Factor V Leiden, Antithrombin III deficiency, Protein C deficiency, Protein S deficiency, Prothrombin gene mutation (G20210A), Hyperhomcysteinemia, antiphospholipid antibody syndrome (APS), anticardiolipin antibody (ACLA) thrombosis syndrome, or lupus anticoagulant (LA) syndrome. In still another embodiment or further embodiment of any of the foregoing, the antibody or antibody fragment is administered within 72 hours after an ischemic event. In still another embodiment or further embodiment of any of the foregoing, the antibody or antibody fragment is administered continuously after an ischemic event. In still another embodiment or further embodiment of any of the foregoing, the administering results in a reduction in ischemia reperfusion injury or inflammation from an ischemic event. In still another embodiment or further embodiment of any of the foregoing, the method further comprises administering one or more additional agents useful to treat ischemia. In a further embodiment, the one or more additional agents are selected from the group consisting of a reperfusion agent, a free-radical scavenger agent, and a spin trap agent, a neuroprotective agent, an anticoagulant, an antiplatelet agent, nimodipine and naloxone. In still another embodiment or further embodiment of any of the foregoing, the method further comprises administering one or more agents useful to treat a thrombotic disorder. In a further embodiment, the one or more agents useful to treat a thrombotic disorder are selected from the group consisting of an anticoagulant, heparin, a vitamin K antagonist, 4-hydroxycoumarin derivatives, warfarin, acenocoumarol, dicumarol, ethyl biscoumacetate, phenprocoumon, streptokinase, urokinase, tissue plasminogen activator (tPA), alteplase (recombinant tPA), reteplase, tenecteplase and argatroban. In still another embodiment or further embodiment of any of the foregoing, the administering results in a reduction in inflammation from the ischemic event. In still another embodiment or further embodiment of any of the foregoing, the antibody or antibody fragment is administered intravascularly. In still another embodiment or further embodiment of any of the foregoing, the $V_H$ domain comprises an amino acid sequence that includes CDRs comprising SEQ ID NO:6, 7 and 8, and/or the $V_L$ domain comprises an amino acid sequence that includes CDRs comprising SEQ ID NO:9, 10 and 11, or SEQ ID NO:10, 11 and 12. In another embodiment, the antibody or antibody fragment is selected from the group consisting of: (a) an antibody or scFv with heavy and light chain domains comprising the complementarity determining regions of SEQ ID NO:6, 7, 8, 9, 10 and 11; and (b) an antibody or scFv with heavy and light chain domains comprising the complementarity determining regions of SEQ ID NO:6, 7, 8, 10, 11 and 12. In still another embodiment, the antibody fragment comprises a single chain variable fragment ("scFv") that recognizes a phosphocholine headgroup of an oxidized phospholipid. In a further embodiment, the scFv is soluble under physiological conditions. In still a further embodiment, the scFv comprises a light-chain variable region having a sequence that is at least 95% identical to the sequence as set forth in SEQ ID NO:2 from amino acid 34 to about amino acid 146. In yet a further embodiment, the scFv comprises a heavy chain variable region having a sequence that is at least 95% identical to the sequence as set forth in SEQ ID NO:2 from about amino acid 162 to about amino acid 284. In still yet a further embodiment, the scFv comprises a light-chain variable region having a sequence that is at least 95% identical to the sequence as set forth in SEQ ID NO:4 from amino acid 24 to about amino acid 135. In a further embodiment, the scFv comprises a heavy chain variable region having a sequence that is at least 95% identical to the sequence as set forth in SEQ ID NO:4 from about amino acid 151 to about amino acid 273. In another or further embodiment, the scFv comprises a sequence that is at least 95% identical to the sequence as set forth in SEQ ID NO:2. In yet another or further embodiment, the scFv comprises a sequence that is at least 95% identical to the sequence as set forth in SEQ ID NO:4 from amino acid 1 to about amino acid 273.

DESCRIPTION OF DRAWINGS

FIG. 2 shows the nucleotide (SEQ ID NO:1) and amino acid (SEQ ID NO:2) sequence and annotations of an scFv of the disclosure.

DETAILED DESCRIPTION

Figure 1A:
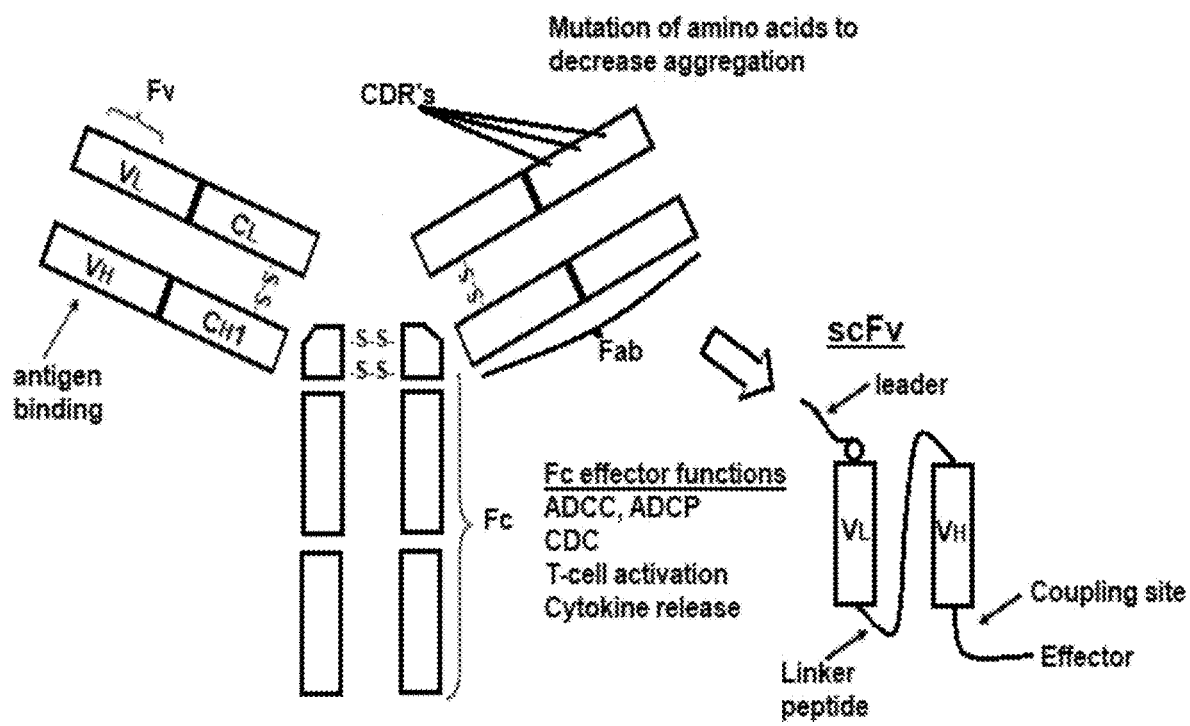
FIG. 1A-B provides (A) a diagram of the process used to produce single-chain variable fragment ("scFv") of the disclosure. As indicated, site directed mutagenesis was employed to mutate the variable domain of the heavy chain ("$V_H$") of a double chain immunoglobulin antibody to increase the solubility of scFv. Linker, leader, and effector regions of the scFv are also indicated (right). (B) Provides a generalized map demonstrating the layout of the genetic components that encode an scFv E06 antibody fragment (top); and a generalized vector map indicating the coding sequence for the E06-scFv antibody fragment in relation to other vector elements that was used to generate transgenic mice (bottom).

As used herein and in the appended claims, the singular forms "a," "an," and "the" include plural referents unless the context clearly dictates otherwise. Thus, for example, reference to "a single-chain variable fragment" or "a scFv" includes a plurality of single-chain variable fragments and reference to "the oxidized phospholipid" includes reference to one or more oxidized phospholipids and equivalents thereof, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Ischemia and reperfusion injury are physiologically different events and do not necessarily occur at the same time. Ischemia generally refers to deficiency of blood to a body part or tissue typically due to a thrombus or embolus. Reperfusion injury results when the obstruction or constriction is removed and is caused by oxidative damage and inflammatory responses.

Tissues deprived of blood and oxygen suffer ischemic necrosis or infarction, often resulting in permanent tissue damage. Cardiac ischemia is often termed "angina", "heart disease", or a "heart attack", and cerebral ischemia is often termed a "stroke". Both cardiac and cerebral ischemia result from decreased blood and oxygen flow which is often followed by some degree of brain damage, damage to heart tissue, or both. The decrease in blood flow and oxygenation may be the result of occlusion of arteries, rupture of vessels, developmental malformation, altered viscosity or other quality of blood, or physical traumas. Diabetes is a risk factor for ischemia.

Loss of blood flow to a particular vascular region is known as focal ischemia; loss of blood flow to the entire brain, global ischemia. When deprived of blood, and thus, oxygen and glucose, brain tissue may undergo ischemic necrosis or infarction. The metabolic events thought to underlie such cell degeneration and death include: energy failure through ATP depletion; cellular acidosis; glutamate release; calcium ion influx; stimulation of membrane phospholipid degradation and subsequent free-fatty-acid accumulation; and free radical generation.

Myocardial ischemia occurs when the heart muscle does not receive an adequate blood supply and is thus deprived of necessary levels of oxygen and nutrients. A common cause of myocardial ischemia is atherosclerosis, which causes blockages in the blood vessels (coronary arteries) that provide blood flow to the heart muscle. Congestive heart failure (CHF) can also result from myocardial infarction followed by cardiac remodeling.

Reperfusion is followed by an intense burst of reactive oxygen species (ROS) that results in cellular dysfunction, inflammation and ultimately cardiomyocyte death by modifying intracellular molecules, including lipids. One target for ROS are the abundant phosphatidylcholine-containing phospholipids molecules that comprise the cellular bilayer within mammalian cells. Oxidation of phosphocholine containing phospholipids results in the formation of OxPL ("OxPL", as used herein and defined below, refers to oxidized phosphocholine containing OxPL). This results in fragmentation of polyunsaturated fatty acids at the sn-2 position, altering conformation of the phosphocholine head group, allowing it to be recognized by innate pattern recognition receptors (PRRs) such as macrophage scavenger receptors CD-36 and SR-B1 and TLRs, soluble proteins such as CRP and natural antibodies (NAbs), such as E06. OxPL potentiate oxidative stress and trigger inflammation, and have been broadly implicated in many inflammatory diseases including atherosclerosis, lung injury, and age related macular degeneration.

As a specific example of the biological activity of OxPL, a brief exposure of human aortic endothelial cells (HAECs) or murine macrophages to OxPL results in changes in transcription of >1,000 genes involved in inflammation, pro-coagulant activity, redox reaction, sterol metabolism, cell cycle, unfolded protein response and angiogenesis. Furthermore, the murine IgM natural antibody E06, which recognizes and bind OxPL, but not unoxidized PL, neutralize OxPL pro-inflammatory effects. In culture, E06 prevented the uptake of oxidized LDL (OxLDL) by macrophages, and attenuated the inflammatory effects of OxPL on endothelial cells and monocytes, while immunization-induced increased titers of E06 were associated with attenuated atherosclerosis in a mouse model of atherosclerosis.

Without being bound by a particular theory, oxidized phospholipids (OxPL) (phospholipids with a phosphocholine (PC) headgroup) are highly pro-inflammatory and proatherogenic and are both induced by and propagate oxidative damage and inflammation. They are present in a wide spectrum of inflammatory diseases, including atherosclerosis, rheumatoid arthritis, diabetic nephropathy, CNS diseases including multiple sclerosis, and a spectrum of acute and chronic pulmonary diseases. For example, OxPL are present in the lungs of both mice and humans infected with a wide variety of viral and bacterial pathogens. OxPL are abundant in bronchial alveolar lavage (BAL) of mice with these infections as well as in acute respiratory distress syndrome following acid installation, or in BAL of mice with COPD secondary to smoking. OxPL are proinflammatory mediators for macrophages, by inducing IL-6 for example, or alternatively inhibit the capacity of macrophages to phagocytize bacteria. OxPL are prevalent in livers of patients and mice with NASH, and have been shown to be involved in the pathogenesis in murine models of NASH. OxPL are also extensively present in atherosclerotic lesions, and in vulnerable plaques of human coronary arteries. They are also released into the circulation during interventional procedures such as PCI and stenting, where they likely mediate downstream proinflammatory and vasoactive effects.

Innate natural antibodies (NAbs) provide the first line of host defense against common oxidation-specific epitopes (OSE) on endogenous neo-epitopes (OxLDL and apoptotic cells) and exogenous epitopes of pathogens, and maintain host homeostasis. OSEs are ubiquitous, formed in many inflammatory tissues, including atherosclerotic lesions, and are a major target of IgM NAbs. The prototypic IgM NAb E06, binds to the phosphocholine (PC) headgroup in oxidized phospholipids (OxPL), and blocks uptake of OxLDL by macrophages. A murine IgM natural antibody to OxPL that binds to the phosphorylcholine ("PC") headgroup of OxPL but not to native, non-oxidized phospholipids ("PL") has been cloned and characterized. However, antibodies like IgM Nab E06 have limited solubility and cannot be readily synthesized.

E06 is an IgM antibody originally cloned from the spleens of Apoe$^{-/-}$ mice. E06 has an identical T15 idiotype as found in an IgA that was first identified for its ability to specifically recognize the phosphocholine component of the cell wall polysaccharide of Streptococcus pneumoniae. The IgA was shown to provide optimal protection against lethal infection with S. pneumonia, a feature which likely strengthened positive selection for both antibodies. In contrast to cellular PRRs, E06 neutralized the pro-inflammatory effects of OxPL, prevented cellular binding of OxLDL by CD36, inhibited OxLDL uptake by macrophages, and prevented OxPL containing apoptotic cells from activating endothelial cells to bind monocytes. Moreover, augmented levels of T15/E06 achieved by direct infusion or immunization with Streptococcal extract reduced atherosclerosis (a lipid and inflammatory disease) in mouse models.

Epidemiologic studies have also suggested that IgM autoantibodies recognizing phosphocholine containing OSE are cardioprotective, with titers inversely associated with incident CVD, angiographic CAD, stroke, and carotid intimal thickness. IgM autoantibodies to OSE decline with age and loss of these protective antibodies may reflect a cause of increased risk of cardiovascular disease with advanced age. Of relevance, the Prognosis and Risk in Acute Coronary Syndromes in Sweden (PRACSIS) study evaluated the prognostic value of serum anti-phosphocholine IgM in a cohort of 1185 subjects presenting with ACS (42% with STEMI). At 18 months of follow-up, individuals with anti-phosphocholine IgM titers lower than the cohort median had a 1.79 fold increase risk (95% confidence interval [CI]: 1.31 to 2.44; p=0.0002) for MI, stroke, acute revascularization, and cardiovascular death (MACE) compared to those with titers above the median. Anti-phosphocholine IgM titers were not associated with MACE in the more contemporary ATLAS ACS-TIMI 46 trial, which enrolled 3,356 subjects with ACS (53% with STEMI) and followed them for 6 months. Several differences between PRACSIS and ALTAS-TIMI, including patient population and composition of background medical therapy are likely to have contributed to the discordant results in these two trials. More importantly, OSE IgMs experience a significant rise and fall in the first 120 days following an MI, and delayed sample collection in ATLAS-TIMI 46 (within 7 days of presentation) may be less representative of steady state IgM levels compared to PRACSIS (samples collected within 24 hours of presentation). It is also important to consider that neither trial directly evaluated IR, which is exemplified in the treatment of the STEMI subset of ACS patients. Finally, therapeutic use of OSE-directed antibodies would likely require significantly larger doses than might be represented by titers of endogenous OSE autoantibodies.

The duality of OSE IgMs, while capable of neutralizing pro-inflammatory OSE such as OxPL, but which could also effectively activate complement via the classical pathway, may also contribute to variable clinical outcomes. Blockade of the complement system is protective against IR in animal models, demonstrating its relevance to IR injury. Immunodeficient Rag$^{-/-}$ mice, which lack B and T cells and therefore do not make antibodies, are protected from IR injury, but infusion of CM22, a monoclonal IgM that recognizes non-muscle myosin heavy chain type II (NMHCII), reconstitutes IR injury that is associated with colocalized IgM and complement bound to injured tissue. Furthermore, both a synthetic peptide derived from NMHCII that competes for CM22 binding and an F(ab')2 that binds NMHCII but lacks a Fc domain and is incapable of fixing complement, reduces myocardial IR injury in mice as well as diminished complement C3 detected in injured myocardium. These findings provide a paradigm for how certain IgMs could exacerbate IR injury by activating complement and potentiating an inflammatory response.

The parent E06 antibody is a murine IgM antibody that was cloned and characterized and which is the subject of U.S. Pat. No. 6,225,070, which is incorporated herein by reference. U.S. Patent Publication No. 20150376268A1 describes a fully functional single chain antibody and humanized antibodies that bind to OxPL. It describes the numerous unique molecular changes to the DNA sequence of the parent antibody framework regions, heavy and light chains, and a linker sequences that was determined by repeated rounds of experimentation, which resulted in the development of a fully functional E06-scFv. When this sequence was inserted into the appropriate vector, the resultant scFv is expressed in a soluble form, and possesses all the immunological binding properties of the parent toward its identified target antigens, including the ability to bind to a unique anti-idiotypic antibody, AB1-2, whose epitopes consists of both the heavy and light chains of the parent antibody. The disclosure of that application also provides for single chain variable antibody fragments ("scFv"), $V_H$, $V_L$ and complementarity determining regions that selectively bind to oxidized phospholipids. The scFvs of the disclosure are soluble and can be readily synthesized. The disclosure of U.S. Pat. Publ. No. 20150376268A1 is incorporated herein by reference for all purposes.

An advantage of the E06-scFv described herein and present in the transgenic mice used in the in vivo experiment is that it can bind and neutralize OxPL, but lacks an Fc domain and therefore cannot bind and active complement. Considering the totality of the available pre-clinical and clinical evidence, the E06-scFv provides a therapy for reducing IR injury.

Myocardial ischemia-reperfusion results in generation of radical oxygen species (ROS) via non-enzymatic mitochondrial dysfunction as well as enzymatic production by xanthine oxidase (from nearby endothelial cells) and NADPH (from infiltrating neutrophils and monocytes), which in turn mediate lipid peroxidation. PC-containing phospholipids, the most abundant class of cellular membrane phospholipids, are prone to oxidative damage from ROS as well as during apoptosis, resulting in formation of OxPL. In addition to direct lethal effects on cardiomyocytes demonstrated in this study, OxPL represents a subset of oxidation specific epitopes (OSE) that are recognized by the innate immune system as danger associated molecular patterns (DAMPs) and promote sterile inflammation. As described elsewhere herein, OxPLs have profound pro-inflammatory effects on monocytes, macrophages and endothelial cells resulting in release of chemokines (MCP-1, fibronectin, and CXCL8) and cytokines (IL-1β, IL-6, and IL-8), and that specific OxPL species (e.g., POVPC and PGPC) had direct pro-apoptotic effects on cells, all of which can contribute to ischemic-reperfusion (IR) injury.

The disclosure provides compositions and methods useful for inhibiting and treating reperfusion injury. The disclosure demonstrates that antibodies and antibody fragments that bind oxidation specific epitopes (OSEs), either alone or in combination with other agents, are useful for treating reperfusion injury and have therapeutic benefit. The disclosure provides methods and compositions useful for inhibiting reperfusion injury and/or tissue damage associated with thrombolism and/or myocardial infarction comprising, for example, administering an antibody or antibody fragment that binds to OSEs and reduces the inflammatory response induced by the OSEs during the ischemic event, or alternatively after the ischemic event, but before reperfusion has occurred, or alternatively after the ischemia and at the time of reperfusion.

The disclosure shows that myocardial ischemia-reperfusion results in a significantly increased production of OxPL in primary cardiomyocyte cell culture in vitro as well as in myocardial tissue in vivo. In cell culture, exposure to exogenously added OxPL, particularly PONPC and POVPC, resulted in cardiomyocyte cell death in the absence of ischemia-reperfusion. E06, a well-characterized IgM natural antibody that specifically recognizes fragmented OxPL such as PONPC and POVPC, but which does not recognize unoxidized PC containing phospholipids, abolished OxPL mediated cell death in vitro and attenuated ischemic-reperfusion infarct size in vivo.

The disclosure thus shows that E06 prevented OxPL mediated cell death in vitro and attenuated IR infarct size in vivo. Thus, targeting OxPL in general, and specifically with an antibody that has the binding specificity of E06, can be an effective pharmacologic therapy to reduce IR injury.

The disclosure shows that constitutive expression of E06-scFv resulted in durable protection against IR injury, with reduced infarct size (e.g., limited adverse cardiac remodeling) 1 week after IR, demonstrating strong clinical translation. The E06-scFv can be administered to the patient or subject in an acute healthcare setting following, or suspected of having, an MI or stroke. In other embodiments an E06-scFv can be administered intravenously post thrombolytic therapy or by intracoronary route during percutaneous coronary intervention (PCI).

There is currently a need for medical therapy to prevent or reduce the oxidative damage and reperfusion injury during and following an ischemic event. The disclosure demonstrates that administration of antibody and antibody fragments (including scFvs) that bind to OSEs reduce injury during ischemic events. In one embodiment, the antibody or antibody fragment has reduced or no complement activating activity.

The disclosure provides use of antibodies, antibody fragments and humanized antibodies that bind to OxPL and which in some instances have the same or similar binding specificity as the E06 antibody. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to tissue. In an acute setting, the half-life of antibody fragments is not critical. For a review of certain antibody fragments, see Hudson et al. (2003) Nat. Med. 9:129-134. In one embodiment, the disclosure provides the use of anti-OxPL antibodies and fragments (e.g., scFv-E06) to treat ischemia and reperfusion injury. The disclosure demonstrates that treating a subject, or tissue, involved in an ischemic event with an anti-OxPL antibody or fragment reduces tissue damage due to inflammation and/or oxidative damage. In another embodiment, the antibody or antibody fragment lacks a region (e.g., an Fc region) that induces complement or recruitment of inflammatory cells.

The disclosure, although providing specific antibody sequences and antibody sequence fragments having biological activity, further disclose that these sequence can be used to generate improved variants. Accordingly, in some instances an antibody or antibody fragment may have a percent identity to the sequences of the disclosure. In other embodiments, the antibody or antibody fragments have specificity for OSEs (e.g., OxPL) but lack the ability to induce complement or recruit inflammatory cells.

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

The disclosure provides an antibody or antibody fragment capable of binding to OxPL or phosphorylcholine and/or a phosphorylcholine conjugate, wherein the antibody or antibody fragment comprises a variable heavy chain ($V_H$) domain and/or a variable light chain ($V_L$) domain, and wherein:

(a) the V$_H$ domain comprises an amino acid sequence that includes one, two or three complementarity determining regions (CDRs) selected from the group consisting of:
(i) SEQ ID NO:6 and sequence that are at least 95%, 96%, 97%, 98%, 99% or 99.9% identical to SEQ ID NO:6, wherein an antibody or fragment thereof comprising such sequence(s) binds to an OSE or OxPL;
(ii) SEQ ID NO:7 and sequence that are at least 95%, 96%, 97%, 98%, 99% or 99.9% identical to SEQ ID NO:7, wherein an antibody or fragment thereof comprising such sequence(s) binds to an OSE or OxPL; and
(iii) SEQ ID NO:8 and sequence that are at least 95%, 96%, 97%, 98%, 99% or 99.9% identical to SEQ ID NO:8, wherein an antibody or fragment thereof comprising such sequence(s) binds to an OSE or OxPL;
(b) the V$_L$ domain comprises an amino acid sequence that includes one, two or three complementarity determining regions (CDRs) selected from the group consisting of:
(i) SEQ ID NO:9 or 12 and sequence that are at least 95%, 96%, 97%, 98%, 99% or 99.9% identical to SEQ ID NO:9 or 12, wherein an antibody or fragment thereof comprising such sequence(s) binds to an OSE or OxPL;
(ii) SEQ ID NO:10 and sequence that are at least 95%, 96%, 97%, 98%, 99% or 99.9% identical to SEQ ID NO:10, wherein an antibody or fragment thereof comprising such sequence(s) binds to an OSE or OxPL; and
(iii) SEQ ID NO:11 and sequence that are at least 95%, 96%, 97%, 98%, 99% or 99.9% identical to SEQ ID NO:11, wherein an antibody or fragment thereof comprising such sequence(s) binds to an OSE or OxPL.

In one embodiment, the antibody or antibody fragment comprises a V$_H$ domain that comprises an amino acid sequence that includes CDRs comprising SEQ ID NO:6, 7 and 8, and/or the V$_L$ domain comprises an amino acid sequence that includes CDRs comprising SEQ ID NO:9, 10 and 11, or SEQ ID NO:10, 11 and 12, wherein an antibody or fragment thereof comprising such sequence(s) binds to an OSE or OxPL.

In one embodiment, the disclosure provides an antibody or an scFv selected from the group consisting of: (a) an antibody or scFv with heavy and light chain domains comprising the complementarity determining regions of SEQ ID NO:6, 7, 8, 9, 10 and 11; and (b) an antibody or scFv with heavy and light chain domains comprising the complementarity determining regions of SEQ ID NO:6, 7, 8, 10, 11 and 12. In one embodiment either of (a) or (b) are linked to an Fc region. In one embodiment, the Fc domain does not induce complement or inflammatory cell recruitment and/or is modified to eliminate complement induction or inflammatory recruitment.

In one embodiment, the disclosure provides an antibody comprising a light-chain variable region as set forth in SEQ ID NO:2 from amino acid 1 to about 146. In another embodiment, the disclosure provides an antibody with a humanized light chain variable region comprising the sequence of SEQ ID NO:4 from amino acid 1 to about 135. In another embodiment, the disclosure provides an antibody that comprises a heavy chain variable region comprising a sequence of SEQ ID NO:2 from about 162 to about 269. In another embodiment, the disclosure provides an antibody that comprises a humanized heavy chain variable region comprising a sequence of SEQ ID NO:4 from about 152 to about 258.

In another embodiment, the disclosure provides a chimeric antibody comprising, for example, a murine VH and/or VL and a human Fc region. For example, SEQ ID NO:14 provides the sequence of a chimeric antibody of the disclosure. In SEQ ID NO:14 amino acids 1-33 comprise and Ig kappa chain leader sequence for antibody secretion; amino acid 34-146 comprise an E06 light-chain variable region; amino acids 147-161 provide a flexible linker sequence; amino acids 162-284 provide an E06 heavy-chain variable region with a triple mutation of P201A, S224A and A225D relative to the wild-type urine E06 antibody; amino acids 285-517 comprise an Fc region, in SEQ ID NO:14 the Fc region is a human IgG1-Fc with a modification of C290S and H294Y to increase ADCC activity. SEQ ID NO:14 also provide a further linker and His tag sequence, which one of skill in the art are optional (e.g., SEQ ID NO:14 from amino acid 518 to 528). The disclosure also contemplates and provides a coding sequence for SEQ ID NO:14 comprising SEQ ID NO:13. One of skill in the art can readily identify the nucleic acid sequence corresponding to the various domains identified above. The disclosure also includes a chimeric antibody sequence that is at least 90%, 95%, 96%, 97%, 98%, 99% or 99.9% identical to SEQ ID NO:14 from amino acid 1 to 284 linked to an Fc region from an different immunoglobulin (e.g., IgA, IgD, IgE, IgG, and IgM, or any of the subclasses (isotypes), e.g., IgG$_1$, IgG$_2$, IgG$_3$, IgG$_4$, IgA$_1$, and IgA$_2$).

In one embodiment, the disclosure provides an scFv comprising a linker between the light change variable region and the heavy-chain variable region. The linker can be any number of commonly used peptide linkers. In one embodiment, the linker comprises a repeating unit of GGGS (SEQ ID NO:5). The repeat of GGGS (SEQ ID NO:5) may be 2, 3, 4 or more times.

In another embodiment, the disclosure comprises a scFv comprising a light chain variable region of SEQ ID NO:2 from amino acid 1 to 146 linked by a peptide linker to a heavy chain variable region of SEQ ID NO:2 from amino acid 162 to about 269. In a specific embodiment, the scFv comprises a sequence of SEQ ID NO:2 form amino acid 1 to 269. In another embodiment, the disclosure provides for an scFv which has a polypeptide sequence of SEQ ID NO:2 from amino acid 1 to about 269 or 1 to about 303. In a further embodiment, the disclosure provides for an scFv that has a polypeptide sequence that has at least 75%, at least 80%, at least 85%, at least 90%, at least 95%, at least 98%, or at least 99% sequence identity to SEQ ID NO:2 from amino acid 1 to about 303 and which selectively binds to an oxidized phospholipid.

In yet further embodiments, fusion constructs comprising a first domain comprising SEQ ID NO:2 from amino acid 1 to about 269 or 1 to about 303 or a variant thereof is operably linked to a second domain comprising (i) a detectable label or (ii) a polypeptide of interest. One of skill in the art will recognize that such fusion constructs can be generated using chemical or molecular biology techniques that link a coding sequence comprising a sequence of SEQ ID NO:1 or variant thereof with a coding sequence of, for example, a polypeptide of interest. The coding sequences and domains may be separated by a linker or directly linked.

In yet another embodiment, the disclosure comprises a scFv comprising a light chain variable region of SEQ ID NO:4 from amino acid 1 to 135 linked by a peptide linker to a heavy chain variable region of SEQ ID NO:4 from amino acid 152 to about 258. In a specific embodiment, the scFv comprises a sequence of SEQ ID NO:4 form amino acid 1 to 258. In another embodiment, the disclosure provides for an scFv which has a polypeptide sequence of SEQ ID NO:4 from amino acid 1 to about 258 or 1 to about 263. In a further embodiment, the disclosure provides for an scFv that has a polypeptide sequence that has at least 75%, at least 80%, at least 85%, at least 90%, at least 95%, at least 98%, or at least 99% sequence identity to SEQ ID NO:4 from amino acid 1 to about 258 and which selectively binds to an oxidized phospholipid.

In yet further embodiments, fusion constructs comprising a first domain comprising SEQ ID NO:4 from amino acid 1 to about 258 or 1 to about 264 or a variant thereof is operably linked to a second domain comprising (i) a detectable label or (ii) a polypeptide of interest. One of skill in the art will recognize that such fusion constructs can be generated using chemical or molecular biology techniques that link a coding sequence comprising a sequence of SEQ ID NO:3 or variant thereof with a coding sequence of, for example, a polypeptide of interest. The coding sequences and domains may be separated by a linker or directly linked.

Nucleic acid molecules encoding the amino acid sequences of the antibodies, antibody fragments and variants of the antibody are prepared by a variety of methods known in the art. For preparing variants such methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

In a particular embodiment, the disclosure provides for a murine scFv which is encoded by a polynucleotide sequence of SEQ ID NO:1. In a further embodiment, the disclosure provides for a murine scFv which is encoded by a polynucleotide sequence that has at least 75%, at least 80%, at least 85%, at least 90%, at least 95%, at least 98%, or at least 99% sequence identity to SEQ ID NO:1 and which produces a polypeptide that selectively binds to an OSE or OxPL.

The disclosure also encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies. See, e.g., Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In a particular embodiment, the disclosure provides for a humanized scFv which is encoded by a polynucleotide sequence of SEQ ID NO:3. In a further embodiment, the disclosure provides for a humanized scFv which is encoded by a polynucleotide sequence that has at least 75%, at least 80%, at least 85%, at least 90%, at least 95%, at least 98%, or at least 99% sequence identity to SEQ ID NO:3 and which produces a polypeptide that selectively binds to an OSE or OxPL.

The disclosure further provides for a scFv disclosed herein that optionally comprises a fragment crystallizable region ("Fc") of an antibody. In a particular embodiment, the Fc region is from a human or humanized antibody. The Fc region is the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and $\alpha$-2,6 linked sialic acid residues. The other part of an antibody, called the Fab region, contains variable sections that define the specific target that the antibody can bind. The scFv of the disclosure are comprised of elements from the Fab region. By contrast, the Fc region of all antibodies in a class are the same for each species; they are constant rather than variable. The Fc region is, therefore, sometimes termed the "fragment constant region". Accordingly, the polynucleotide and polypeptide sequences which encode the Fc regions for countless species have already been determined and would be known by one of skill in the art. In a particular, embodiment, the disclosure provides for an scFv polynucleotide sequence disclosed herein (i.e., SEQ ID NO:1) that further comprises a polynucleotide sequence which encodes an Fc region from IgG antibody (e.g., from a human IgG antibody). In a further embodiment, the disclosure provides for an scFv polypeptide sequence disclosed herein (i.e., SEQ ID NO:2 from amino acid 1 to about 303) that further comprises a polypeptide sequence of an Fc region from an IgG antibody. In yet a further embodiment, the Fc region is modified to remove a biological activity selected from inflammatory cell recruitment and/or complement activation.

In a particular, embodiment, the disclosure provides for a scFv polynucleotide sequence disclosed herein (i.e., SEQ ID NO:3 from 1 to about 789). In a further embodiment, the disclosure provides for an scFv polypeptide sequence disclosed herein (i.e., SEQ ID NO:4 from amino acid 1 to about 258 or about 1 to 263). SEQ ID NO:4 further provides a polypeptide sequence of an Fc region from an IgG antibody (e.g., SEQ ID NO:4 from about amino acid 264 to about 506), this sequence may be absent, partially or fully present.

In a further embodiment, the disclosure provides for a vector which comprises a polynucleotide sequence encoding a scFv as set forth above with reference to SEQ ID NO:1 and 3 or sequences having sequence identity of at least 99%, at least 95%, at least 90%, at least 85%, at least 80%, at least 75% or at least 70% identity to SEQ ID NO:1 or SEQ ID NO:3 and which encodes a polypeptide that specifically binds to an OSE or oxidized phospholipid (OxPL).

The disclosure also provides a humanized antibody that has the binding specificity of an E06 antibody. The humanized antibody comprises (i) a sequence as set forth in SEQ ID NO:4 from amino acid 1 to about amino acid 506 or (ii) a sequence that is at least 90%, 91%, 92%, 93%, 94%, 95%, 96%, 97%, 98%, 99%, 99.5%, 99.8% or more identical to SEQ ID NO:4 from amino acid 1 to about 506 and which encodes a polypeptide that specifically binds to an OSE or oxidized phospholipid (OxPL).

The disclosure also provide a polynucleotide that encodes a humanized antibody of the disclosure. The polynucleotide comprises a sequence selected from the group consisting of (i) a polynucleotide that encodes SEQ ID NO:4, (ii) a polynucleotide that hybridizes under stringent conditions to a polynucleotide consisting of SEQ ID NO:3 and encodes a humanized antibody that binds to OSEs and/or OxPL with a specificity substantially similar to the E06 antibody, (iii) a polynucleotide that is at least 90%, 91%, 92%, 93%, 94%, 95%, 96%, 97%, 98%, 99%, 99.5%, 99.8% or more identical to SEQ ID NO:3 and which encodes an antibody that binds to OSEs and/or OxPL with a specificity substantially similar to the E06 antibody; (iv) a polynucleotide as set forth in SEQ ID NO:3 and (v) a polynucleotide of any of (i) to (iv) wherein the polynucleotide comprises RNA.

Polynucleotide sequences encoding polypeptide components of the antibody or antibody fragments of the disclosure can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. Coli* is typically transformed using pBR322, a plasmid derived from an *E. Coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage vectors may be utilized in making a recombinant vector which can be used to transform susceptible host cells such as *E. Coli* LE392.

The expression vector of the disclosure may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the (3-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In another embodiment, the production of the antibody/antibody fragments according to the disclosure can occur in the cytoplasm of the host cell, and therefore does not require the presence of secretion signal sequences within each cistron. In that regard, antibody light and heavy chains are expressed, folded and assembled to form functional immunoglobulins within the cytoplasm. Certain host strains (e.g., the *E. Coli* trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the disclosure include Archaebacteria and Eubacteria, such as Gram-negative or Gram-positive organisms. Examples of useful bacteria include *Escherichia* (e.g., *E. Coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. Coli* cells are used as hosts for the disclosure. Examples of *E. Coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 (U.S. Pat. No. 5,639,635). Other strains and derivatives thereof, such as *E. Coli* 294 (ATCC 31,446), *E. Coli* B, *E. ColiX* 1776 (ATCC 31,537) and *E. Coli* RV308 are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. Coli, Serratia*, or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the disclosure are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures.

In one embodiment, the expressed polypeptides (e.g., antibody or fragments thereof) are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Large scale or small scale fermentation can be used and can be optimized using skills well known in the art.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration.

The disclosure further provides for an expression vector which encodes a scFv or humanized antibody disclosed herein that is transferred into a suitable host organism. The suitable host organism is a microorganism, yeast or a mammalian cell system. Typically, the mammalian cell system is monocyte-derived (e.g., macrophages, monocytes, and neutrophils), lymphocyte-derived (e.g., myeloma, hybridoma, and a normal immortalized B cell), parenchymal (e.g., hepatocytes) and non-parenchymal cells (e.g., stellate cells).

The disclosure provides a method of treating patients with a scFv (humanized or non-humanized) of the disclosure or a human or humanized antibody of the disclosure or other small molecules presenting a thrombic event, myocardial infarction and/or ischemic event. In one embodiment, the method includes administering an antibody (or fragment thereof) of the disclosure (e.g., scFv-E06) within a minute to a few minutes (e.g., 2, 3, 4, 5, 6, 7, 8, 9, 10, 11, 12, 13, 14, 15, 20, 25, 30, 35, 40, 45, 50, or 55 minutes) to an hour or several hours (e.g., 1, 2, 3, 4, 5, 6, 7, 8, 9 or 10 hours). Typically, the antibody will be administered acutely and as soon as possible after a myocardial infarction, thrombotic event or ischemic injury. The antibody will typically be administered to the affected tissue or into the circulation (e.g., IV). The antibody inhibits the effects of OSEs and/or oxidized phospholipids on the tissue effected by the ischemic injury, infarct or thrombosis.

As described above and below, the scFvs disclosed herein bind to OSEs and/or OxPLs and block their pro-inflammatory effects. The in vivo use of a scFv (humanized or non-humanized) of the disclosure or a humanized antibody of the disclosure can be used to block OSEs and/or OxPL biological effects in many different situations. For example, it has been shown that OxPLs are released from atherosclerotic coronary arteries when these arteries are undergoing surgical procedures to implant and/or expand stents. These released OxPLs could bring about adverse vasoactive effects throughout the patient's body. Acute and/or chronic injection/infusion of a scFv (humanized or non-humanized) of the disclosure or a humanized antibody of the disclosure therefore could block these adverse effects and/or alternatively block or attenuate similar ischemic events, such as acute coronary syndromes or acute strokes. Similarly, a scFv (humanized or non-humanized) of the disclosure or a humanized antibody of the disclosure could also be infused to a subject so as to block proinflammatory effects mediated by OxPLs generated from a variety of pathological conditions, such as respiratory distress secondary to chemical, viral or bacterial infection, or in acute exacerbations of chronic obstructive pulmonary disease ("COPD") where OxPLs have been shown to impair macrophage clearance of bacterial infections. Accordingly, a scFv (humanized or non-humanized) of the disclosure or a humanized antibody of the disclosure would be effective anti-inflammatory agents in other systemic inflammatory settings such as in rheumatoid arthritis, or by inhibiting the inflammatory events associated with NASH and NAFLD. Accordingly, a scFv (humanized or non-humanized) of the disclosure or a humanized antibody of the disclosure can be used in many clinical applications or settings where anti-inflammatories and/or anti-atherosclerotic agents need to be administered temporally and/or chronically. Further, by the fact that E06-scFv was expressed from macrophages provides for the use of a scFv (humanized or non-humanized) of the disclosure or a humanized antibody of the disclosure in strategies to provide sustained systemic expressed levels of a scFv (humanized or non-humanized) of the disclosure or a humanized antibody of the disclosure in humans.

Thus, the antibodies, antibody fragments and polypeptides of the disclosure can be used to treat inflammatory diseases and disorders, cardiovascular diseases, and diseases associated with oxidized phospholipids. More particularly, the antibodies, antibody fragments and polypeptides of the disclosure can be used to treat ischemic-reperfusion injury resulting from disease or physical trauma (e.g., surgical, accidental injury etc.). The term cardiovascular diseases, is intended to include but is not limited to atherosclerosis, acute coronary syndrome, acute myocardial infarction, myocardial infarction (heart attack), stable and unstable angina pectoris, aneurysms, coronary artery disease (CAD), ischemic heart disease, ischemic myocardium, cardiac and sudden cardiac death, cardiomyopathy, congestive heart failure, heart failure, stenosis, peripheral arterial disease (PAD), intermittent claudication, critical limb ischemia, and stroke.

In other embodiments, the disclosure provides a method of treating, preventing, or ameliorating acute kidney injury (AKI) in a subject comprising administering to the subject antibodies and antibody fragments that bind to OSEs, including MAA and/or OxPL, thereby treating, preventing, or ameliorating acute kidney injury. In certain embodiments, the subject's kidney is hypoxic. In certain embodiments, the acute kidney injury is caused by renal ischemia. In certain embodiments, the renal ischemia is caused by cardiac-mediated hypoperfusion. In certain embodiments, the cardiac-mediated hypoperfusion is caused by cardiac surgery, such as bypass surgery, coronary artery bypass grafting, valvular surgery, or combined coronary artery bypass grafting and valvular surgery. It has been estimated that acute renal failure occurs in up to 30% of patients who undergo cardiac surgery and is associated with morbidity and mortality. Furthermore, dialysis is required in approximately 1% of all cardiac surgery patients, most of whom remain dependent on dialysis long-term. Rosner et al., Clin J Am Soc Nephrol. 2006 January; 1(1):19-32.

In another embodiment, the disclosure provides for administering to the subject or patient having impaired renal function an antibody or antibody fragment that binds to OSE, including MAA and/or OxPL, wherein such administration improves renal function. In certain embodiments, administering to the subject or patient at risk of acute kidney injury an antibody or antibody fragment that binds to OSE, including MAA and/or OxPL preventing tubular epithelial cell injury in the subject. In certain embodiments, administering to the subject or patient at risk of acute kidney injury an antibody or antibody fragment that binds to OSE, including MAA and/or OxPL improves, or prevents the decline of, glomerular filtration rate (GFR). In certain embodiments, administering to the subject or patient at risk of acute kidney injury an antibody or antibody fragment that binds to OSE, including MAA and/or OxPL, decreases, or prevents the increase of, levels of blood urea nitrogen (BUN) and/or creatinine, which are markers of renal function that increase with impaired renal function. In other embodiments, the disclosure provides for administering to the subject or patient at risk of acute kidney injury an antibody or antibody fragment that binds to OSE, including MAA and/or OxPL, prevents increases of neutrophil gelatinase-associated lipocalin (NGAL) and/or kidney injury molecule 1 (KIM-1), which are urinary biomarkers whose levels positively correlate with AKI.

In other embodiments, the disclosure provides a method of decreasing plasma levels of OSE, including MAA or OxPL, in a subject having, or at risk of having, acute kidney injury (AKI) comprising administering to the subject or patient at risk of acute kidney injury an antibody or antibody fragment that binds to OSE, including MAA and/or OxPL, thereby decreasing plasma levels of OSE in the subject. In certain embodiments, the subject's kidney is hypoxic. In certain embodiments, the acute kidney injury is caused by renal ischemia. In certain embodiments, the renal ischemia is caused by cardiac-mediated hypoperfusion. In certain embodiments, the cardiac-mediated hypoperfusion is caused by cardiac surgery, such as bypass surgery, coronary artery bypass grafting, valvular surgery, or combined coronary artery bypass grafting and valvular surgery. In certain embodiments, the renal ischemia is caused by gastric bypass surgery, orthotopic liver transplant, abdominal aortic aneurysm repair, contrast agent induced hypoxia, or drug induced hypoxia.

The disclosure also provides a method of reducing or inhibiting tubular epithelial cell injury in the kidney of a subject having, or at risk of having, acute kidney injury comprises administering to the subject an antibody or antibody fragment that binds to OSE, including MAA and/or OxPL to the subject, thereby reducing or inhibiting tubular epithelial cell injury in the kidney of the subject. In certain embodiments, the subject's kidney is hypoxic. In certain embodiments, the acute kidney injury is caused by renal ischemia. In certain embodiments, the renal ischemia is caused by cardiac-mediated hypoperfusion. In certain embodiments, the cardiac-mediated hypoperfusion is caused by cardiac surgery, such as bypass surgery, coronary artery bypass grafting, valvular surgery, or combined coronary artery bypass grafting and valvular surgery. In certain embodiments, the renal ischemia is caused by gastric bypass surgery, orthotropic liver transplant, abdominal aortic aneurysm repair, contrast agent induced hypoxia, or drug induced hypoxia.

The disclosure provides a method of preventing or protecting a subject from acute kidney injury comprises administering to the subject an antibody or antibody fragment that binds to OSE, including MAA and/or OxPL, prior to, during or after the subject undergoes cardiac surgery. In certain embodiments, a method of preventing or protecting a subject from acute kidney injury comprises administering to the subject an antibody or antibody fragment that binds to OSE, including MAA and/or OxPL, prior to, during or after the subject undergoes cardiac surgery. In certain embodiments, a method of preventing or protecting a subject from acute kidney injury comprises identifying a subject in need of cardiac surgery and administering to the subject an antibody or antibody fragment that binds to OSE, including MAA and/or OxPL, prior to, during or after the subject undergoes cardiac surgery. In certain embodiments, the cardiac surgery is bypass surgery, coronary artery bypass grafting, valvular surgery, or combined coronary artery bypass grafting and valvular surgery.

The disclosure also provides a method of administering to the subject an antibody or antibody fragment that binds to OSE, including MAA and/or OxPL, prior to, during or after the subject undergoes cardiac surgery to prevent acute kidney injury, protect against acute kidney injury, minimize acute kidney injury, or reduce acute kidney injury in the subject following cardiac surgery. In certain embodiments, an antibody or antibody fragment that binds to OSE, including MAA and/or OxPL, is administered multiple times prior to, during or after the subject undergoes cardiac surgery.

The disclosure also provides a method of preventing or protecting a subject from acute kidney injury comprises administering an antibody or antibody fragment that binds to OSE, including MAA and/or OxPL, to the subject prior to, during or after the subject undergoes a surgery or operation that causes renal ischemia. In certain embodiments, a method of preventing or protecting a subject from acute kidney injury comprises identifying a subject in need of surgery or operation and administering an antibody or antibody fragment that binds to OSE, including MAA and/or OxPL, to the subject prior to, during or after the subject undergoes surgery or operation. In certain embodiments, the surgery or operation is gastric bypass surgery, orthotopic liver transplant, or abdominal aortic aneurysm repair. In certain embodiments, administering an antibody or antibody fragment that binds to OSE, including MAA and/or OxPL, to the subject prior to, during or after the subject undergoes surgery or operation is sufficient to prevent acute kidney injury, protect against acute kidney injury, minimize acute kidney injury, or reduce acute kidney injury in the subject following surgery or operation. In certain embodiments, the antibody or antibody fragment that binds to OSE, including MAA and/or OxPL, is administered multiple times prior to, during or after the subject undergoes surgery or operation.

The disclosure provides a method of preventing or protecting a subject from acute kidney injury comprises administering to the subject an antibody or antibody fragment that binds to OSE, including MAA and/or OxPL, prior to, during or after administering a drug that induces ischemia. In certain embodiments, a method of preventing or protecting a subject from acute kidney injury comprises identifying a subject in need of a drug known to induce ischemia and administering to the subject an antibody or antibody fragment that binds to OSE, including MAA and/or OxPL, prior to, during or after administering the drug known to induce ischemia. In certain embodiments, administering to the subject an antibody or antibody fragment that binds to OSE, including MAA and/or OxPL, prior to, during or after administering a drug known to induce ischemia is sufficient to prevent acute kidney injury, protect against acute kidney injury, minimize acute kidney injury, or reduce acute kidney injury in the subject following administration of the drug known to induce ischemia. In certain embodiments, the antibody or antibody fragment that binds to OSE, including MAA and/or OxPL, is administered multiple times prior to administering the drug known to induce ischemia. Several types of drugs that induce ischemia are known in the art. Non-limiting examples include cyclosporine A and its structural analogues; angiotensin converting enzyme (ACE) inhibitors, such as, but not limited to, Benazepril, Captopril, Enalapril, Fosinopril, Lisinopril, Moexipril, Perindopril, Quinapril, Ramipril, and Trandolapril; and non-steroidal anti-inflammatory drugs (NSAIDs), such as, but not limited to, Aspirin (acetylsalicylic acid), Diflunisal, Salsalate, Ibuprofen, Dexibuprofen, Naproxen, Fenoprofen, Ketoprofen, Dexketoprofen, Flurbiprofen, Oxaprozin, Loxoprofen, Indomethacin, Tolmetin, Sulindac, Etodolac, Ketorolac, Diclofenac, Nabumetone, Piroxicam, Meloxicam, Tenoxicam, Droxicam, Lornoxicam, Isoxicam, Mefenamic acid, Meclofenamic acid, Flufenamic acid, Tolfenamic acid, and Celecoxib. Certain embodiments provide a PHD1 specific inhibitor for treating, preventing, or ameliorating acute kidney injury. In certain embodiments, the acute kidney injury is caused by hypoxia. In certain embodiments, the acute kidney injury is caused by renal ischemia. In certain embodiments, the renal ischemia is caused by cardiac-mediated hypoperfusion. In certain embodiments, the cardiac-mediated hypoperfusion is caused by cardiac surgery, such as bypass surgery, coronary artery bypass grafting, valvular surgery, or combined coronary artery bypass grafting and valvular surgery.

The disclosure provides for the use of an antibody or antibody fragment that binds to OSE, including MAA and/or OxPL, for the preparation of a medicament for treating acute kidney injury. In certain embodiments, the acute kidney injury is caused by hypoxia. In certain embodiments, the acute kidney injury is caused by renal ischemia. In certain embodiments, the renal ischemia is caused by cardiac-mediated hypoperfusion. In certain embodiments, the cardiac-mediated hypoperfusion is caused by cardiac surgery, such as bypass surgery, coronary artery bypass grafting, valvular surgery, or combined coronary artery bypass grafting and valvular surgery.

The disclosure also provides a method of preventing or protecting a subject from ischemic-reperfusion injury comprising administering an antibody or antibody fragment that binds to OSE, including MAA and/or OxPL, to the subject prior to, during or after the subject undergoes a surgery or operation that causes has a risk of causing ischemic injury. In certain embodiments, the method includes administering an antibody or antibody fragment that binds to OSE, including MAA and/or OxPL, to the subject prior to, during or after the subject undergoes surgery or operation. In certain embodiments, the surgery or operation is gastric bypass surgery, orthotopic liver transplant, cardiac bypass surgery, heart surgery, brain surgery, stent placement or removal, or abdominal aortic aneurysm repair. In certain embodiments, the antibody or antibody fragment that binds to OSE, including MAA and/or OxPL, is administered multiple times prior to, during or after the subject undergoes surgery or operation.

The disclosure also provides a method of preventing or protecting a subject from ischemic-reperfusion injury in a subject that has suffered a heart attack, stroke or other ischemic event, comprising administering an antibody or antibody fragment that binds to OSE, including MAA and/or OxPL, to the subject prior to (e.g., at risk of having), during or after the subject has had heart attack, stroke or ischemic event. In certain embodiments, the antibody or antibody fragment that binds to OSE, including MAA and/or OxPL, is administered multiple times prior to, during or after the ischemic event.

As described herein, heart tissue injury can be induced or can be the result of age related or diseases. As used herein in reference to heart tissue "induced injury" refers to damaged myocardium, such as damage that results from heart surgery, including but not limited to, coronary artery bypass surgery, cardiac transplant and application of a mechanical support device, such as a left ventricular assist device (LVAD).

Therapeutic formulations and compositions comprising an antibody or fragment thereof of the disclosure are prepared by mixing the antibody or fragment having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Various terms are used throughout the application. The following brief descriptions are provided to assist in understanding certain terms, but are not meant to be limiting unless otherwise explicitly stated.

As used herein the phrase "adverse cardiac remodeling" refers to the changes in size, shape, and associated function of the heart after injury to the left and right ventricle and/or right and left atrium. The injury is typically due to acute myocardial infarction (such as, for example transmural or ST segment elevation infarction) or induced injury (such as for example, heart surgery), but may be from a number of causes that result in increased pressure or volume overload (forms of strain) on the heart. Cardiac remodeling includes hypertrophy, thinning of the myocardium, scar formation of the myocardium, atrophy of the myocardium, heart failure progression and combinations thereof. Chronic hypertension, Kawasaki's disease, congenital heart disease with intracardiac shunting, and valvular heart disease may lead to remodeling. Additionally remodeling may stem from coronary artery bypass surgery, cardiac transplant and application of a mechanical support device, such as a left ventricular assist device (LVAD).

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments. An antibody can be human, humanized and/or affinity matured. In specific embodiments an antibody of the disclosure binds to OSEs and/or OxPL with a binding specificity the same as or substantially similar to E06 antibodies. In certain embodiments, an antibody of the disclosure comprises a binding domain comprises the CDRs of E06 antibody.

Depending on the amino acid sequence of the constant domain of a heavy chain, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion typically retains at least one, more commonly most or all, of the functions normally associated with that portion when present in an intact antibody. Examples of antibody fragments include Fab, Fab', F(ab')$_2$, and Fv fragments; diabodies; linear antibodies; single-chain antibody molecules (e.g., scFv); and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as antibody half-life modulation. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment. It should be recognized however, a long half-life of the antibody is not necessary for certain indication (e.g., acute ischemic/reperfusion treatments). In certain embodiments of the disclosure a specific example of an antibody fragment binds to OSEs and/or OxPL. In further embodiments, an antibody fragment comprises an scFv-E06 fragment.

An "antigen" is a predetermined antigen to which an antibody can selectively bind. The target antigen may be polypeptide, carbohydrate, nucleic acid, lipid, hapten or other naturally occurring or synthetic compound. In one embodiment, of the disclosure an antigen comprises an OSE. In another embodiment, the antigen is an OxPL.

The term "anti-OSE antibody" refers to an antibody that is capable of binding to an OSE on a molecule with sufficient affinity such that the antibody is useful as a diagnostic and/or therapeutic agent in targeting molecules with OSEs. In some embodiments of the disclosure an anti-OSE antibody has the same or a similar binding specificity and $K_d$ as the E06 antibody.

The term "anti-OxPL antibody" or "an antibody that binds to OxPL" refers to an antibody that is capable of binding to an OxPL with sufficient affinity such that the antibody is useful as a diagnostic and/or therapeutic agent in targeting OxPL. In some embodiments of the disclosure an anti-OxPL antibody has the same or a similar binding specificity and $K_d$ as the E06 antibody. In still another embodiment, an anti-OxPL antibody binds to the PC headgroup of OxPLs.

A "blocking" antibody or an "antagonist" antibody is one which inhibits or reduces biological activity of the antigen it binds. Certain blocking antibodies or antagonist antibodies substantially or completely inhibit the biological activity of the antigen. For example, an anti-OSE antibody or an anti-OxPL antibody of the disclosure and block the biological activity of an oxidation specific epitope in inducing inflammation.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the disclosure.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like. Biological samples may be collected from a subject having or suspected of having an ischemic or ischemic-reperfusion event in order to determine the level of OSEs before, during and after treatment.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993). Triabodies and tetrabodies are also described in Hudson et al., Nat. Med. 9:129-134 (2003). For example, a diabody of the disclosure can comprise a first binding domain derived from and E06 antibody and a second binding domain having an affinity for OSEs which comprise a different sequence than the first domain or a second binding domain that binds to a distinct target different from an OSE.

A "disorder" or "disease" is any condition that would benefit from treatment with a substance/molecule or method of the disclosure. This includes acute ischemic events and related pathological conditions.

An "effective amount" refers to an amount effective, at dosages and for periods of time necessary, to achieve the desired therapeutic or prophylactic result, such as reduction in ischemic-reperfusion injury, oxidative damage, apoptosis and/or tissue damage.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the $V_H$-$V_L$ dimer. As is known in the art, the six HVRs confer antigen-binding specificity to an antibody. However, even a single variable domain (or half of an Fv comprising only three HVRs specific for an antigen) has the ability to recognize and bind antigen.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains have a free thiol group. F(ab')$_2$ antibody fragments originally were produced as pairs of Fab' fragments which have hinge cysteines between them. Other chemical couplings of antibody fragments are also known.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584). See also, for example, Li et al., Proc. Natl. Acad. Sci. USA, 103:3557-3562 (2006) regarding human antibodies generated via a human B-cell hybridoma technology. It should be important to note that a "human antibody" does not include naturally occurring antibodies produced by a human, but rather refer to antibodies that do not contain any epitope or antigenic fragment a human subject would not recognize as "foreign".

The term "hypervariable region," "HVR," or "HV," (note these are sometimes referred to "complementarity determining regions" or "CDRs") when used herein refers to the regions of an antibody variable domain which are hypervariable in sequence and/or form structurally defined loops. Generally, antibodies comprise six HVRs; three in the $V_H$ domain (H1, H2, H3), and three in the $V_L$ domain (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

As used herein, an "ischemia/reperfusion event" includes, but is not limited to, myocardial ischemia, myocardial reperfusion, subarachnoid hemorrhage, ischemic strokes (including strokes resulting from cerebral thrombosis, cerebral embolism, and atrial fibrillation), hemorrhagic strokes (including strokes resulting from aneurysm and arteriovenous malformation), and transient ischemic attack, cardiac surgery where a heart lung machine is used such as coronary artery bypassing, and preservation of organs for transplant.

As used herein "ischemia/reperfusion injury" refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The "light chains" of antibodies (immunoglobulins) from any vertebrate species can be assigned to one of two clearly distinct types, called kappa (κ) and lambda (λ), based on the amino acid sequences of their constant domains.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier term "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody for purposes of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier term "monoclonal" indicates the character of the antibody as being obtained from a substantially homogeneous population of antibodies, and is not to be construed as requiring production of the antibody by any particular method. For example, the monoclonal antibodies to be used in accordance with the disclosure may be made by a variety of techniques, including, for example, the hybridoma method (e.g., Kohler and Milstein, Nature, 256: 495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include antibodies wherein the antigen-binding region of the antibody is derived from an antibody produced by, e.g., immunizing macaque monkeys with the antigen of interest.

"Oligonucleotide," as used herein, refers to short, typically single stranded polynucleotides that are generally, but not necessarily, less than about 200 nucleotides in length. The terms "oligonucleotide" and "polynucleotide" are not mutually exclusive. The description for polynucleotides is equally and fully applicable to oligonucleotides.

"Oxidized phospholipids (OxPL)" refer to phospholipids with a phosphocholine (PC) headgroup. OxPL are highly pro-inflammatory and proatherogenic. Phosphorylcholine, a polar head group on certain phospholipids, has been extensively implicated in cardiovascular disease. Reactive oxygen species generated during coronary inflammation causes the oxidation of low density lipoprotein (LDL) to generate oxidized LDL (oxLDL). In fact, cardiovascular diseases (CVD) such as atherosclerosis, unstable angina, or acute coronary syndrome have been shown to be associated with elevated plasma levels of oxLDL (Itabe and Ueda. 2007). LDL is a circulating lipoprotein particle that contains lipids with a PC polar head group and proteins, an apoB100 protein.

During oxidation of LDL PC containing neo-epitopes that are not present on unmodified LDL are generated. Newly exposed PC on oxLDL is recognized by scavenger receptors on macrophages, such as CD36, and the resulting macrophage-engulfed oxLDL proceeds towards the formation of proinflammatory foam cells in the vessel wall. Oxidized LDL is also recognized by receptors on endothelial cell surfaces and has been reported to stimulate a range of responses including endothelial dysfunction, apoptosis, and the unfolded protein response (Gora et al. 2010). PC neo-epitopes are also exposed on LDL following modification with phospholipase A2 or amine reactive disease metabolites, such as aldehydes generated from the oxidation of glycated proteins. These alternately modified LDL particles are also pro-inflammatory factors in CVD.

Antibodies towards phosphorylcholine (PC) have been shown to bind oxidized, or otherwise modified, LDL and block the pro-inflammatory activity of oxLDL in in vivo models or in vitro studies (Shaw et al. 2000; Shaw et al. 2001).

"Oxidation specific epitopes (OSEs)" refer to "danger-associated molecular patterns (DAMPs)" that are pro-inflammatory and are integrally involved in oxidative, innate and adaptive immune responses. OSEs include, but are not limited to, OxPL and MDA epitopes. OSEs represent DAMPs that are detrimental to the host, and that the innate immune system provides protective responses to them. Such DAMPs are present on apoptotic cells, infectious pathogens such as pneumococcus and oxidized lipids. In response to such DAMPs, evolutionary processes have preserved and amplified innate immune effector proteins to bind and neutralize their pro-inflammatory effects. The initial evolutionary pressure may have been derived from the need to clear trillions of apoptotic cells on a daily basis, which may have been subsequently amplified by repeated exposure to common infectious pathogens that share similar epitopes or molecular mimics, as well as oxidized lipids derived from the diet and those generated in vivo following oxidative stress.

A "polynucleotide," or "nucleic acid," as used herein, refer to polymers of nucleotides of any length, and include DNA and RNA. The nucleotides can be deoxyribonucleotides, ribonucleotides, modified nucleotides or bases, and/or their analogs that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2T-O-methyl-, 2T-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "purified" antibody or antibody fragment (e.g., scFv) is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and typically more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. An isolated antibody includes the antibody in situ within recombinant cells since at least one component of the antibody's natural environment will not be present. Ordinarily, however, a purified antibody will be prepared by at least one purification step.

As used herein "reduced myocardial infarct size" refers to a decrease in the size of a myocardial infarct in subjects treated with an antibody or antibody fragment compared to the size of a myocardial infarct in control subjects receiving no treatment. In the disclosed methods, "reducing" can refer to about a 5-80% (e.g., any one of a 5%, a 10%, a 20%, a 30%, a 40%, a 50%, a 60%, a 70%, a 80% or any percentage value between any of the foregoing) decrease in myocardial infarct size. As is known to those of skill in the art, changes to the myocardium, particularly determination of the size of a myocardial infarct, can be measured using imaging techniques such as echocardiography, cardiac MRI, cardiac CT, and cardiac nuclear scans. Additionally, elevation of one or more biomarkers, including troponin, CK-MB (creatine kinase mb), and CPK (creatine phosphokinase), is known to be indicative of dead or dying myocardium. There is also evidence that the biomarker BNP (B-type Naturetic Peptide) can be used as a marker for cardiac remodeling.

Therapies are desired that promote or affect favorable cardiac remodeling following cardiac stress or injury. As used herein "favorable cardiac remodeling" refers to preservation of chamber size, shape, function and the prevention of ventricular wall thinning and scarring which occurs after injury to the heart.

Figure 1B:
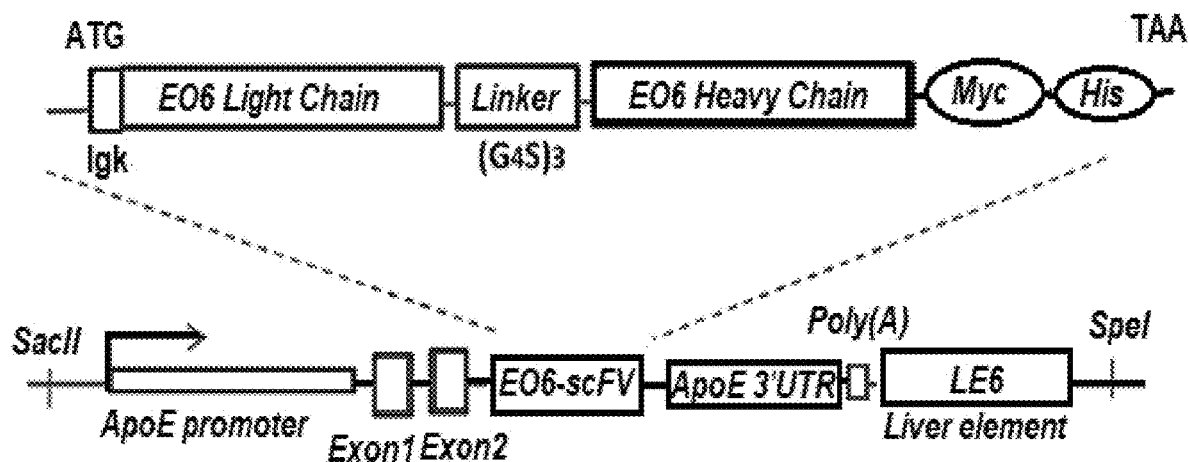

"Single-chain Fv" or "scFv" antibody fragments comprise the V$_H$ and V$_L$ domains of antibody, wherein these domains are present in a single polypeptide chain. Generally, the scFv polypeptide further comprises a polypeptide linker between the V$_H$ and V$_L$ domains which enables the scFv to form the desired structure for antigen binding. FIG. 1 shows an antibody and scFv structure. For a review of scFv see Pluckthun, The Pharmacology of Monoclonal Antibodies, vol. 113, Rosenburg and Moore eds., Springer-Verlag, New York, pp. 269-315 (1994).

The term "substantially similar" or "substantially the same," as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by the values (e.g., $K_d$ values). The difference between said two values is, for example, less than about 50%, less than about 40%, less than about 30%, less than about 20%, less than about 10%, less than about 5%, less than about 2%, or less than about 1% as a function of the reference/comparator value.

The phrase "substantially reduced," or "substantially different," as used herein, denotes a sufficiently high degree of reduction or difference, respectively, between two numeric values (generally one associated with a molecule and the other associated with a reference/comparator molecule) such that one of skill in the art would consider the difference between the two values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

A "therapeutically effective amount" of an antibody or antibody fragment of the disclosure may vary according to factors such as the disease state, age, sex, and weight of the individual, and the ability of the antibody or antibody fragment to elicit a desired response in the individual. A therapeutically effective amount is also one in which any toxic or detrimental effects of the antibody or antibody fragment are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

"Tissue Ischemia" or "tissue ischemic" or "a tissue ischemic condition" refer to a medical event which is pathological in origin, or to a surgical intervention which is imposed on a subject, wherein circulation to a region of the tissue is decreased, impeded or blocked, either temporarily, as in vasospasm or transient ischemic attack (TIA) in cerebral ischemia or permanently, as in thrombolic occlusion in cerebral or cardiac ischemia. The affected region is deprived of oxygen and nutrients as a consequence of the ischemic event. This deprivation leads to the injuries of infarction in the region affected. Ischemia occurs in the brain during, for example, a stroke, cardiac arrest, severe blood loss due to injury or internal hemorrhage and other similar conditions that disrupt normal blood flow. Ischemia occurs in myocardial tissue as a result of, for example, atherosclerosis and CHF. It may also occur after a trauma to the tissue since the pressure caused by edema presses against and flattens the arteries and veins inside the tissue, thereby reducing their ability to carry blood through the tissue. Cerebral ischemia may also occur as a result of macro- or micro-emboli, such as may occur subsequent to cardiopulmonary bypass surgery. As used herein, a "non-cardiovascular" ischemic condition specifically excludes an ischemic condition of the cardio-pulmonary system or circulatory system. As used herein, a "non-cerebral" ischemic condition specifically excludes an ischemic condition of the brain.

A tissue ischemic condition can be selected from the group consisting of cerebral ischemia; intestinal ischemia; spinal cord ischemia; cardiovascular ischemia; myocardial ischemia associated with myocardial infarction; mycardial ischemia associated with CHF, ischemia associated with age-related macular degeneration (AME); liver ischemia; kidney/renal ischemia; dermal ischemia; vasoconstriction-induced tissue ischemia; penile ischemia as a consequence of priapism and erectile dysfunction; ischemia associated with thromboembolytic disease; ischemia associated with microvascular disease; and ischemia associated with diabetic ulcers, gangrenous conditions, post-trauma syndrome, cardiac arrest resuscitation, hypothermia, peripheral nerve damage or neuropathies. In some embodiments, the tissue ischemic condition is cerebral or cardiac ischemia.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, a scFv (humanized or non-humanized) of the disclosure or a humanized antibody of the disclosure are used to delay development of a disease or disorder.

The term "variable", in the context of an antibody binding domain, refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions or hypervariable regions (CDRs or HVRs, used interchangeably herein) both in the light-chain and the heavy-chain variable domains. The more highly conserved portions of variable domains are called the framework (FR). The variable domains of native heavy and light chains each comprise four FR regions, largely adopting a (3-sheet configuration, connected by three HVRs, which form loops connecting, and in some cases forming part of, the (3-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

A "variant Fc region" comprises an amino acid sequence which differs from that of a native sequence Fc region by virtue of at least one amino acid modification, typically one or more amino acid substitution(s). Typically, the variant Fc region has at least one amino acid substitution compared to a native sequence Fc region or to the Fc region of a parent polypeptide, e.g. from about one to about ten amino acid substitutions, and typically from about one to about five amino acid substitutions in a native sequence Fc region or in the Fc region of the parent polypeptide. The variant Fc region of a disclosure possesses at least about 80% homology with a native sequence Fc region and/or with an Fc region of a parent polypeptide, at least about 90% homology therewith, and typically at least about 95% homology therewith.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and replicate along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids.

The following examples are intended to illustrate but not limit the disclosure. While they are typical of those that might be used, other procedures known to those skilled in the art may alternatively be used.

EXAMPLES

Materials. Synthetic standards 1,2-dinonanoyl-sn-glycero-3-phosphocholine (DNPC), 1-palmitoyl-2-(5-oxovaleroyl)-sn-glycero-3-phosphocholine (POVPC), 1-palmitoyl-2-glutaroyl-sn-glycero-3-phosphocholine (PGPC), 1-Palmitoyl-2-azelaoyl-sn-glycero-3-phosphocholine (PAzPC), 1-palmitoyl-2-(9-oxo)nonanoyl-sn-glycero-3-phosphocholine (PONPC), and the IgM murine natural antibody E06, which is LPS free, were obtained from Avanti Polar Lipids (Alabaster, Ala.). 1-(palmitoyl)-2-(5-keto-6-octene-dioyl)-3-phosphocholine (KOdiAPC) and, 1-palmitoyl-2-(4-keto-dodec-3-ene-dioyl)-sn-glycero-3-phosphocholine (KDdiAPC) were purchased from Cayman Chemicals (Ann Arbor, Mich.). All solvents were HPLC grade.

Cell culture of rat cardiomyocytes. All animal experiments performed conform to the NIH guidelines regarding animal experimentation. Neonatal rat cardiomyocytes (NNCM) were isolated from 1-2 day old Sprague-Dawley rat pups. Whole hearts were excised from rat pups by midline sternotomy after cervical dislocation. Hearts were washed and minced to adequately break up macroscopic structures before re-washing with cold filter sterilized phosphate buffered saline (PBS) containing 10 g/L of glucose to remove red blood cells and debris. Repeated enzymatic digestion of heart fragments was performed with collagenase (740U), trypsin (370U), and DNase (2880U) (Worthington Biochemical) agitating at 35° C. for three 10-minute and three 7-minute digestions. Digested supernatant solutions were centrifuged into a cell pellet and then separation of cell types using a Percoll® (GE Healthcare) gradient of 1.05, 1.06, and 1.082 g/mL allowed for a layer enriched with myocytes to be isolated. To remove fibroblasts, the cells were pre-plated on non-coated 150 mm culture plates for 45 min. Purified NNCM (95% pure by sarcomere staining) were then transferred to sterile tissue culture plates at a cell density of $1.75 \times 10^6$/35-mm plate. Collagen-coated glass coverslips in 24-well tissue culture plates were used for microscopy analysis and NNCM were plated at $3.2 \times 10^5$/well. Cells were incubated overnight in Dulbecco's Modified Eagle Medium/Ham's nutrient mixture F-12 (1:1) containing 2 mM glutamine, 3 mM $NaHCO_3$, 15 mM HEPES, and 50 mg/mL gentamycin (DMEM/F12) plus 10% fetal bovine serum (FBS). DMEM/F12 with 10% FBS was changed to serum-free DMEM/F12 (DFSF) the following day. Control solution consisted of 140 mM NaCl, 6 mM KCl, 1.25 mM $CaCl_2$, 6 mM HEPES, and 10 mM D-glucose buffered to pH 7.4, ischemic solution was buffered to pH 6.0, and consisted of the same components, except 8 mM KCl was added and no D-glucose was added. The ischemic buffer was purged of oxygen by bubbling 95% $N_2$ and 5% $CO_2$ gas into the medium for 1 hour before being applied to cells. A hypoxic chamber designed for storage in a 37° C. water jacketed tissue culture incubator was used to maintain an atmosphere of 95% $N_2$ and 5% $CO_2$ gas conditions for 18 hours overnight. Reperfusion was achieved by applying control buffer to cells for 4 hours in a normal culture incubator. After the treatment, cells were scraped off into a small portion of PBS. Cardiomyocyte cell lysates were subjected to Western Blot analysis.

Generation and characterization of E06-scFv transgenic mice. The generation of transgenic C57BL/6 mice expressing the T15/E06 idiotype as a single chain variable antibody fragment—termed E06-scFv-Tg. In brief, the cDNAs encoding E06 variable regions of the heavy and light chains were linked with a 15-amino acid peptide by overlapping PCR, and cloned into an expression vector pSecTag2A (Invitrogen) containing a murine Ig kappa-chain leader sequence for secretion and c-myc and polyHis as epitope tags. HEK293 cells were transfected and the binding properties of E06-scFv secreted into culture supernatant were shown to mimic those of the intact E06. The same construct was then cloned into the liver-specific expression vector pLiv7 and used to generate transgenic (Tg) mice in the C57BL/6 background expressing the E06-scFv transgene driven by the apoE promoter. Offspring were screened both for plasma E06-scFv titer and integration of the transgene by PCR amplification of the tail DNA. The transgenic E06-scFv founder lines were bred with each other to generate "homozygous" transgenic mice, and in turn, these were crossed into $Ldl^{-/-}$ mice on the C57BL/6 background. All animals were genotyped for E06-scFv and $Ldlr^{-/-}$, respectively and plasma assayed to confirm expression of the E06-scFv by immunoassay. The E06-scFv mRNA was strongly expressed in liver, peritoneal macrophages and spleen, and to a lesser extent in heart. Plasma levels of the E06-scFv averaged 20-30 µg/ml in these studies.

Ischemia-reperfusion surgery in rats and mice. Male Sprague-Dawley rats (200 grams) underwent coronary artery ligation. The procedure was performed under anesthesia with 3% isoflurane and oxygen at 2 L/min on a mask. Myocardial ischemia was produced by occlusion of the left anterior descending coronary artery. A 1-1.5 cm lateral thoracotomy incision is made to the left of and parallel to the sternum. The left coronary artery was tied with a 6-0 monofilament suture. In control animals, the suture was placed around the artery but not tied. After 60 min of ischemia, the suture was removed and the heart allowed to reperfuse. The chest was closed in layers and de-aired and the animals were allowed to recover. Post-operative analgesia was provided by subcutaneous buprenorphine at 0.03-0.05 mg/kg at 1 hour post-surgery and every 8 hours after for a total of 3 injections. After 24 hours, the animals were sedated with 3% isoflurane and 2D echocardiographic studies were repeated and subsequently the hearts were removed and 1 mm cross sections made for lipidomic analysis, and triphenyltetrazoliumchloride (TTC) staining. N=10 in each group. For rat studies, only hearts that demonstrated both ECG and 2D echocardiographic evidence of myocardial ischemia were selected for the IR group. To minimize ex vivo lipid peroxidation, immediately after removal from the body, myocardial tissue was immediately flash frozen in liquid nitrogen. The entire heart tissue was pulverized with liquid nitrogen and the resulting tissue underwent Folch extraction in the presence of DNPC (10 ng/100 µl) as internal standard and 0.01% BHT as antioxidant.

Adult (18-20-week-old) E06-scFv-Tg/Ldlr$^{-/-}$ mice or Ldlr$^{-/-}$ mice weighing 16-40 grams, were anesthetized with a mixture of Ketamine (50 mg/kg) and Xylazine (5 mg/kg) and 1.0% isoflurane. Mice were intubated with a pressure ventilator (Kent Scientific, PhysioSuite. Peak inspiration pressure was ~13 cm H$_2$O and inspiration rate 100-110. The skin over the mid thorax was shaved and cleansed with Betadine or Chlorhexidine solution. A skin incision was made from the midsternal line toward the left armpit, and the chest opened with a 1 cm lateral cut along the left side of the sternum, cutting between the 3rd and 4th ribs to expose the left ventricle of the heart. The ascending aorta and main pulmonary artery were identified; the left anterior descending (LAD) coronary artery was located as it traverses the anterior wall of the heart, between the left and right ventricles. LAD coronary artery occlusion was performed by tying an 8-0 prolene suture ligature on a piece of 2-0 silk suture. Occlusion of the artery was assessed by blanching of the territory of perfusion of the LAD coronary artery, along with acute ST segment elevation on limb-lead electrocardiographic leads. Following an ischemic period of 60 minutes, the suture was removed from around the LAD coronary artery. Reperfusion was confirmed by observing return of blood flow in the epicardial coronary arteries.

Histologic assessment of infarct size. One week following surgery, mice were euthanized with terminal anesthesia after intraperitoneal administration of 50 units of heparin. Hearts were immediately harvested, submerged in ice-cold relaxation solution A (120 mmol/L NaCl, 20 mmol/L NaHCO$_3$, 11 mmol/L glucose, 5.4 mmol/L KCl, 1.2 mmol/L MgCl$_2$, 10 mmol/L 2,3-butanedione 2-monoxime). The ascending aorta was cannulated and the hearts were perfused retrogradely via a 21-guage blunted needle connected to a Langendorff perfusion apparatus at 80 mmHg pressure. The suture left around the LAD coronary artery in situ after the ischemia reperfusion surgery was religated and 1% (w/v) Evans blue (EB) dye in solution A was then injected to define area at risk (AAR). Failure in re-occlusion of the coronary artery resulted in exclusion of animals from the final analysis. The heart was then sectioned into 1 mm slices using a heart slicer (Zivic Instruments) and incubated in 1.5% (w/v) triphenyltetrazoliumchloride (TTC) in PBS. With TTC, viable myocardium stains brick red and the infarct appears pale white. The sizes of AAR and infarct area (IA) were quantified by computerized planimetry using ImageJ. The identity of animals remained anonymous to the examiner who carried out staining procedures and area measurements.

OxPL mass spectrometry. PC-containing phospholipids were extracted from NNCM. Cell media was removed, and cells were washed with PBS. Each well was scraped into 1 mL of methanol/acetic acid (3% v/v) solution containing 0.01% BHT and transferred to a 10 mL glass conical tube and capped under N$_2$ (g). Ten nanograms of DNPC was added as internal standard into each sample for quantitation purposes. Two milliliters of hexane containing BHT was added to the tube, capped under N$_2$ (g), vortexed for five seconds, and then centrifuged for 5 min at 3500 rpm at 4° C. The upper hexane layer was then siphoned off using a glass Pasteur pipette and discarded. The hexane/BHT wash was repeated three times, capping under N$_2$ (g), vortexing for five seconds, and centrifuging after each wash. After the final hexane/BHT wash, 2 mL of chloroform containing BHT and 750 µL of PBS were added to the tube then vortexed and centrifuged as described above. The lower organic layer was removed using a glass Pasteur pipette and transferred to a clean 15 mL glass conical tube where the solution was aspirated off using a nitrogen evaporator, and then reconstituted into 300 µL of chloroform/methanol (2:1 v/v) for storage at −80° C.

The separation of OxPLs was carried out using reverse-phase (RP) chromatography. Extracted hearts were reconstituted in RP eluent consisting of 60:40 acetonitrile:water, 10 mM ammonium formate and 0.1% formic acid immediately prior to injection. Thirty microliters of the sample were injected onto an Ascentis Express C18 HPLC column (15 cm×2.1 mm, 2.7 µm; Supelco Analytical, Bellefonte, Pa., USA) with separation by a Prominence UFLC system from Shimadzu Corporation (Canby, Oreg., USA). Elution was performed using a linear gradient of solvent A (acetonitrile/water, 60:40 v/v) and solvent B (isopropanol/acetonitrile, 90:10, v/v) with both solvents containing 10 mM ammonium formate and 0.1% formic acid. The mobile phase composition that was used is as follows: initial solvent B at 32% until 4.00 min; switched to 45% B; 5.00 min 52% B; 8.00 min 58% B; 11.00 min 66% B; 14.00 min 70% B; 18.00 min 75% B; 21.00 min 97% B; 25.00 min 97% B; 25.10 min 32% B. A flow rate of 260 µl/min was used for analysis, and the sample tray and column oven were held at 4 and 45° C., respectively.

Detection of OxPL was carried out by mass spectrometry in positive polarity mode. MRM scans were performed on 6 transitions using a product ion of 184.3 m/z, corresponding to the cleaved phosphocholine moiety. Six commercially available standards of PONPC, POVPC, PGPC, PAzPC, KOdiAPC, and KDdiAPC were injected and accurate peak assignments were based upon retention times and mass transitions. The mass spectrometry settings were as follows: curtain gas, 26 psi; collision gas, medium; ion spray voltage, 5500 V; temperature, 500.0° C.; ion source gas 1, 40.0 psi; ion source gas 2, 30.0 psi; declustering potential, 125 V, entrance potential, 10 V; collision energy, 53 V; collision cell exit potential, 9 V; and dwell time, 50 msec. External mass calibration was performed at regular intervals. For quantitation, multiple reaction monitoring (MRM) calibration curves were made for each of the 6 commercially available OxPL standards and peaks were normalized based on their relative responses. Ten nanograms of internal standard was added to all samples during extraction. A 4000 QTRAP® triple quadrupole mass spectrometer system with a Turbo V electrospray ion source from AB Sciex (Framingham, Mass., USA) was coupled to the liquid chromatography system.

In vitro OxPC treatment and assessment of cell viability. Fresh DFSF was applied to NNCM on glass cover-slips and supplemented with 1, 2, 5, and 10 µM concentrations of OxPL lipids sonicated into PBS, forming micelles. Four OxPL species, POVPC, PONPC, PGPC, and PAzPC were applied to NNCM plates for 4 hours and compared to a non-oxidized PC standard PSPC. Plates were then washed with PBS before NNCM were analyzed for cell viability using vital dyes, calcein-acetoxymethyl ester (AM) and ethidium homodimer-1 (Invitrogen). Mitochondrial permeability after exposure to OxPL molecules was monitored by fluorescence microscopy using a solution of calcein-AM fluorescent dye with cobalt chloride (CoCl$_2$) applied to cardiomyocytes cultured on glass coverslips.

To evaluate the effect of neutralizing OxPL on cell viability, the IgM E06 antibody was used at a concentration of 10

µg/mL within cell culture. The antibody was purchased as 100 µg suspended in 100 µl of PBS suitable for direct application into cell culture. Co-treatment with OxPL was at 5 µM of each OxPL molecule and PSPC for 2 hrs. Cell viability was assessed as described above. All microscopy was done on an Olympus AX70 microscope, with pictures taken using a CoolSnap® camera and Image Pro-Plus 5.1.2 Software. Images were assessed using Adobe Photoshop CS5.1 Software.

Statistical analysis. Student's t-tests were performed comparing each treatment group to control by two-tailed analysis with P<0.05 representing significance. All data is represented as the mean±standard deviation.

Figure 3A:
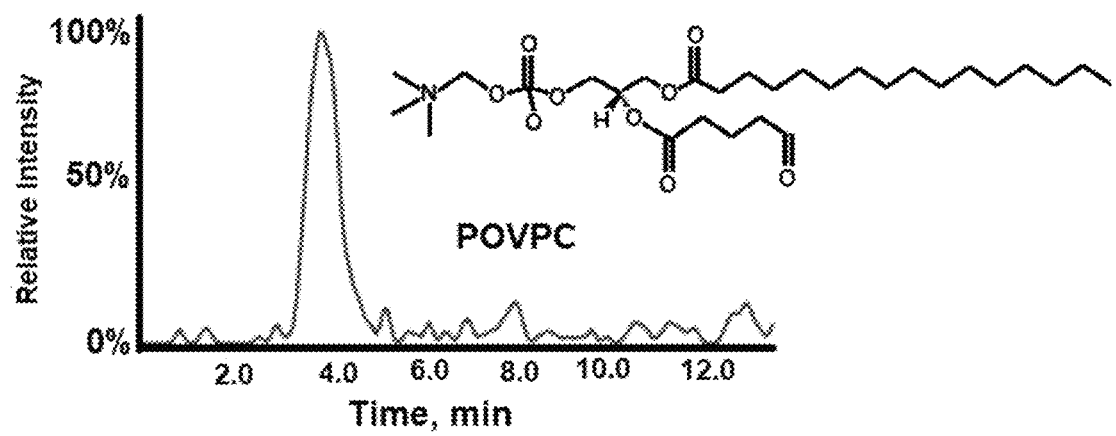
FIG. 3A-F shows identification of fragmented OxPL molecules in NNCM during IR. (A-E) Single MRM ion chromatograms of fragmented OxPL identified in NNCM during IR. Cells were incubated under IR conditions are described in the Methods section. (F) Presence of most abundant OxPL in cultured NNCM after IR compared to control. The most abundant compound was PONPC, which had a significant increase after exposure to IR. N=4 separate cultures, each done in triplicate (*p<0.05).
Figure 3B:
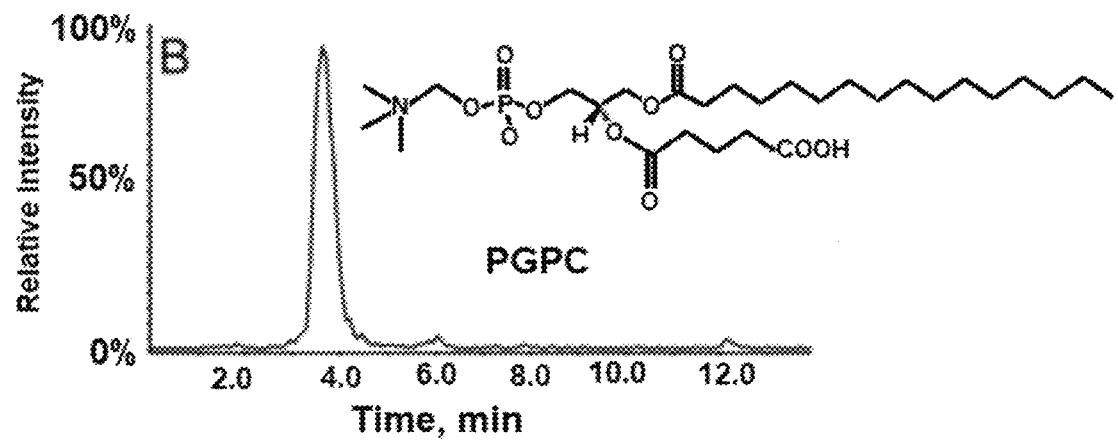
Figure 3C:
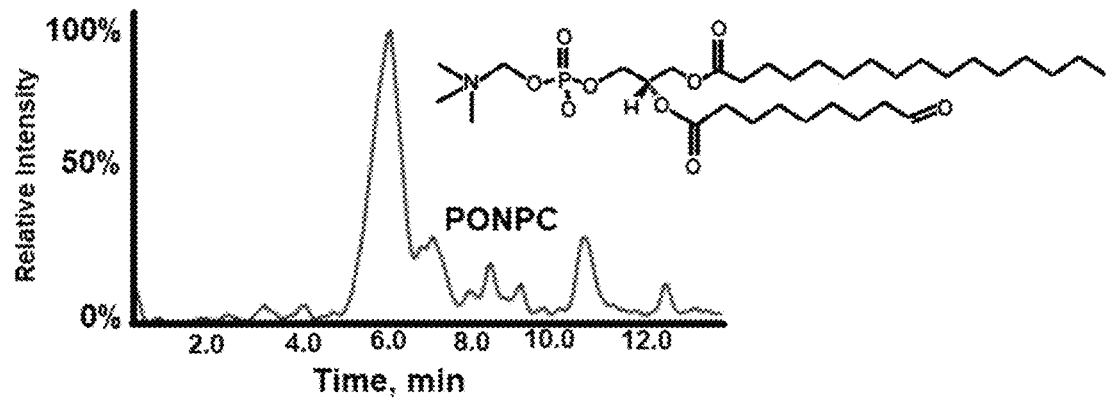
Figure 3D:
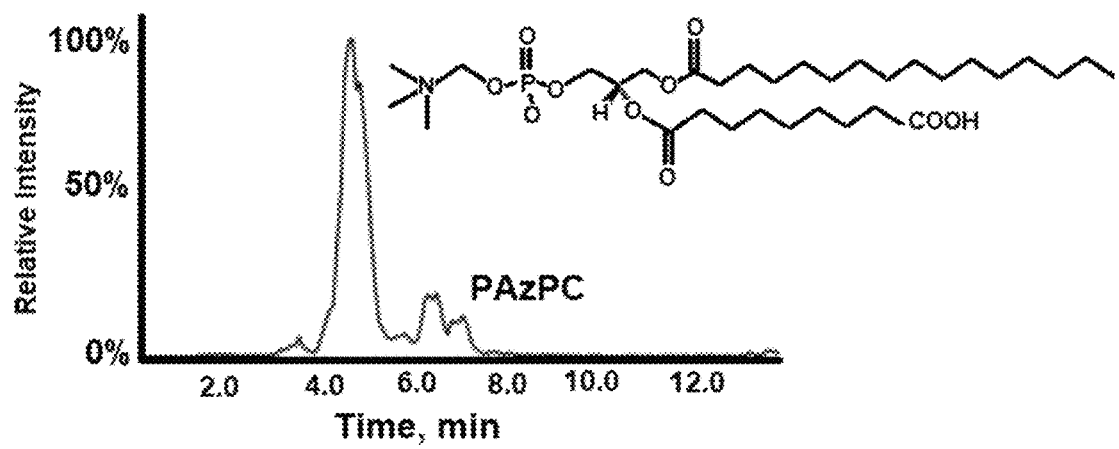
Figure 3E:
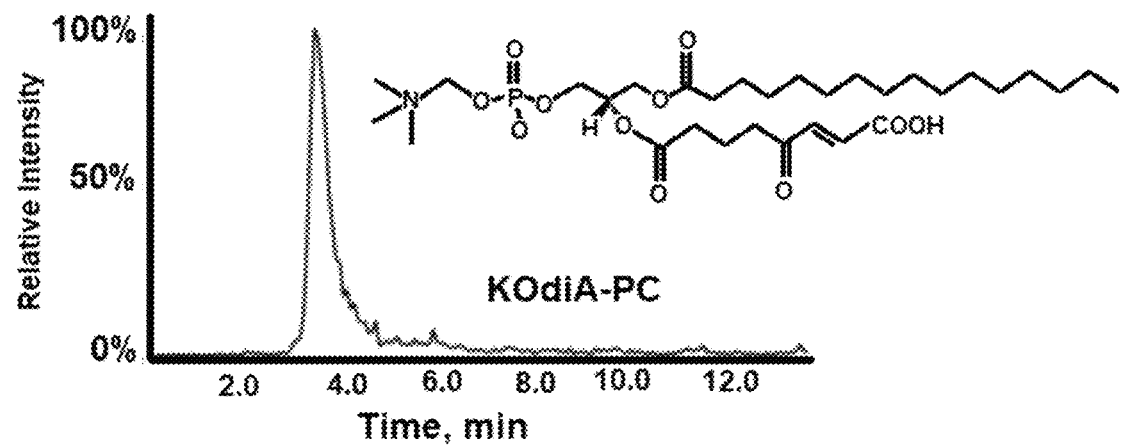
Figure 3F:
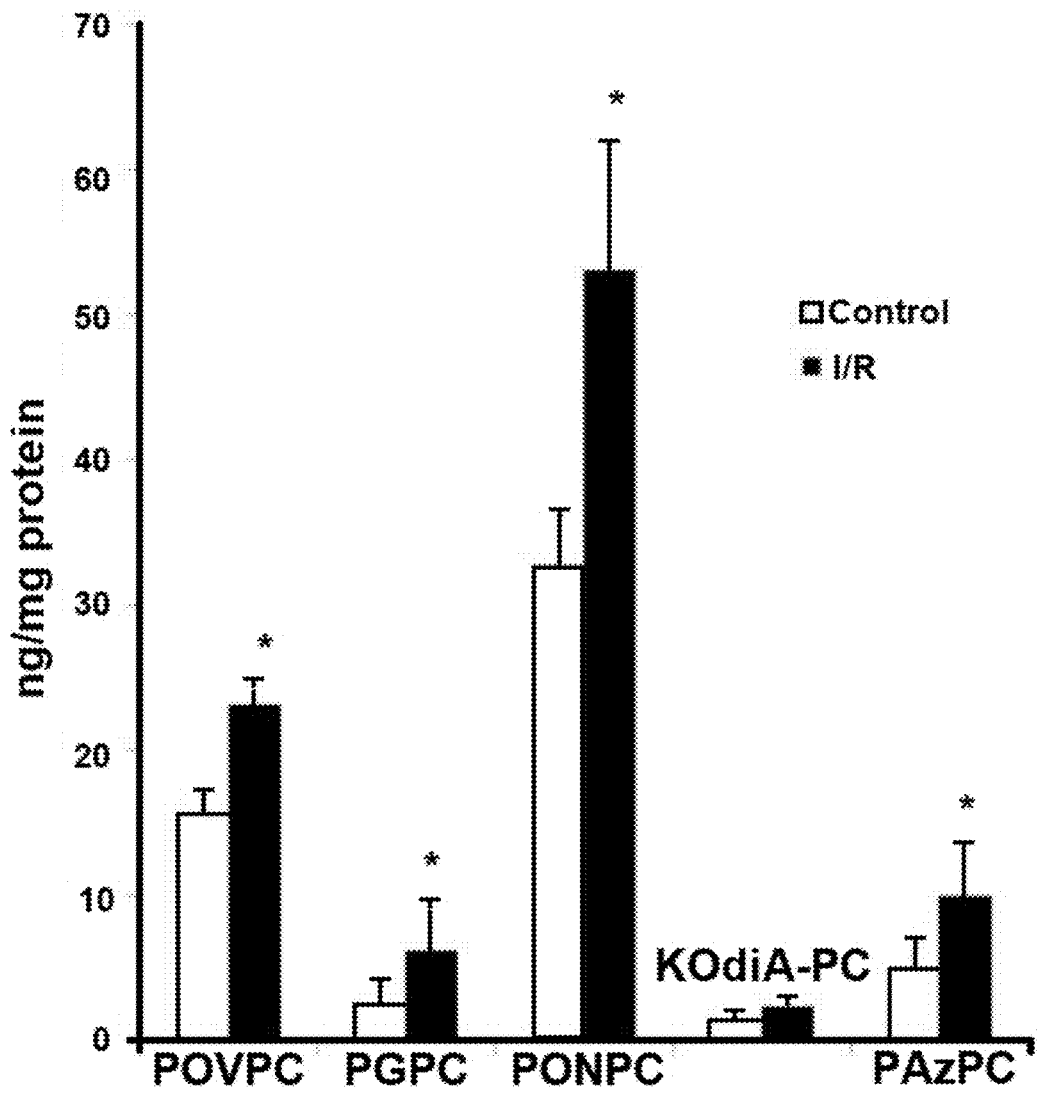

OxPL are Generated in Rat Cardiomyocytes Following IR. Neonatal rat cardiomyocytes (NNCM) exposed to control and IR conditions were analyzed by LC/MS/MS with MRM for the 6 commercially available fragmented OxPL species. Five OxPL molecules POVPC (m/z 594), PGPC (m/z 610), PONPC (m/z 650), PAzPC (m/z 666) and KOdiA-PC (m/z 664) were identified in cell extracts of both control and simulated IR conditions (FIG. 3A-E). There was a significant increase in the generation of 4 of the identified OxPL in NNCM exposed to simulated IR (FIG. 3F). Significant increases were noted in mass of PONPC (32.7±3.2 to 53.0±9.1 ng/mg protein, p<0.001), POVPC (15.6±1.5 to 23.1±1.7 ng/mg protein, p<0.05) PGPC (2.5±1.2 to 6.1±2.1 ng/mg protein, p<0.05), and PAzPC (5.0±1.5 to 9.9±3.8 ng/mg protein p<0.01).

Figure 4A:
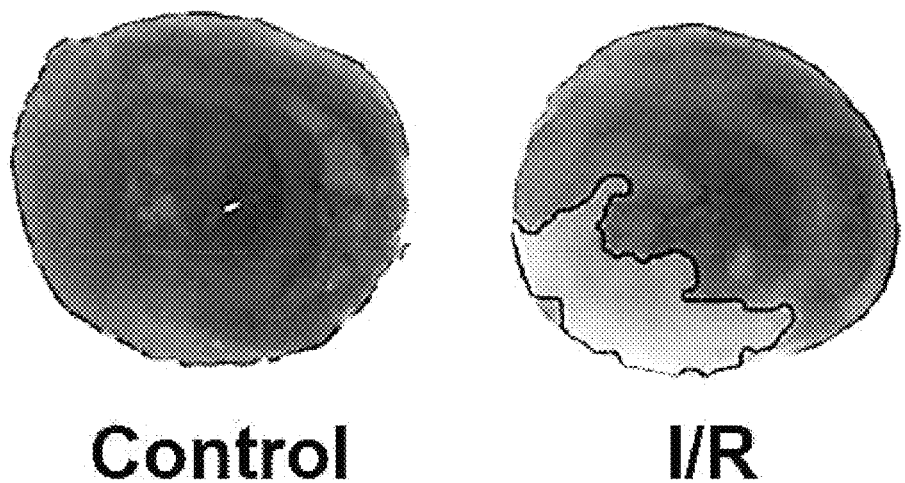
FIG. 4A-B shows changes in OxPL levels during rat coronary ligation IR injury. (A) TTC staining of cross section of rat myocardium in control and after 1 hr of ischemia with 24 hrs of reperfusion. (B) Significant increase in OxPL levels in rat myocardium after 24 hrs of IR injury. n=3 (*p<0.05) N=3 separate experiments with 5 animal each.
Figure 4B:
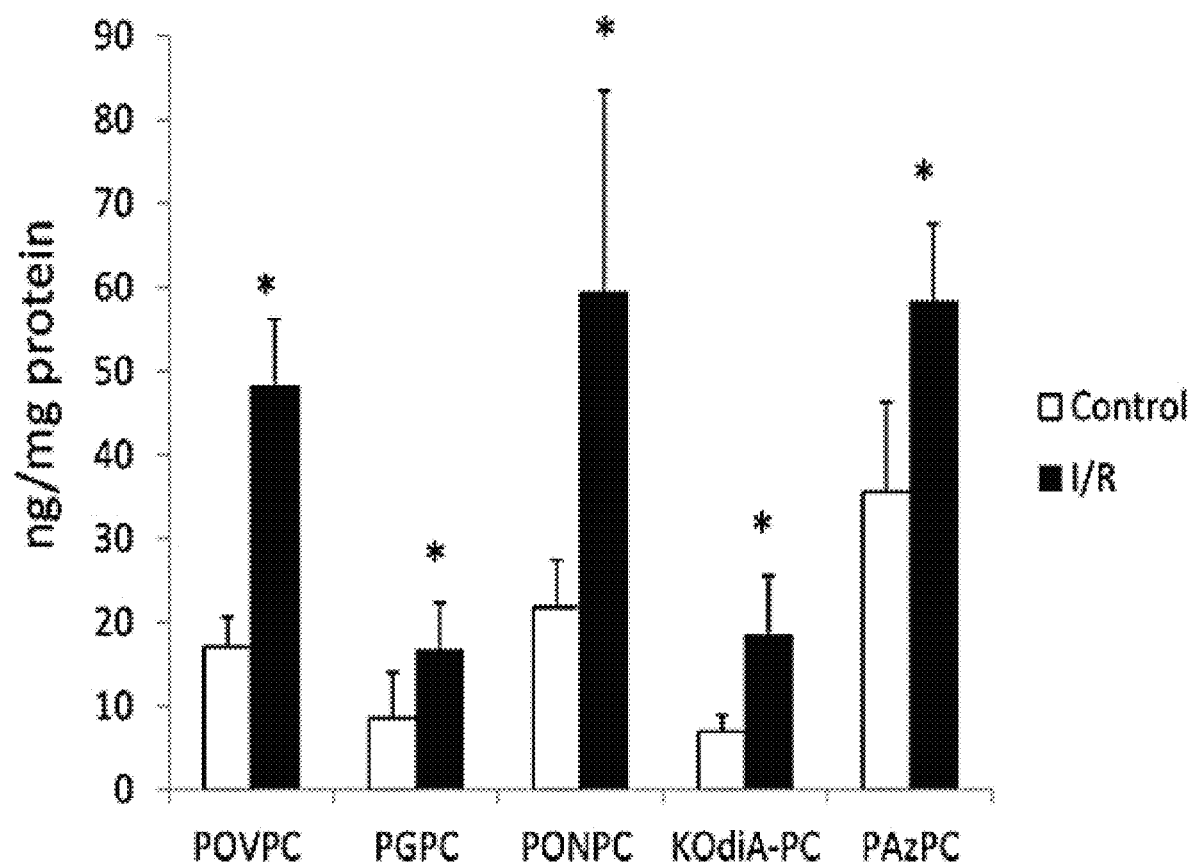

Changes in OxPL that occurred in rat myocardium during coronary IR were investigated. After 1 hour of ischemia and a subsequent 24 hours of reperfusion (FIG. 4A) there were significant increase in 5 of the measured OxPL species within rat myocardium, with PONPC being the most abundant molecules (FIG. 4B). As compared to cardiomyocytes in culture subjected to IR conditions, there was relatively greater enrichment of PAzPC among the identified OxPL species in rat myocardium exposed to IR conditions.

OxPL Causes Rat Cardiomyocyte Cell Death in vitro.

Figure 5A:
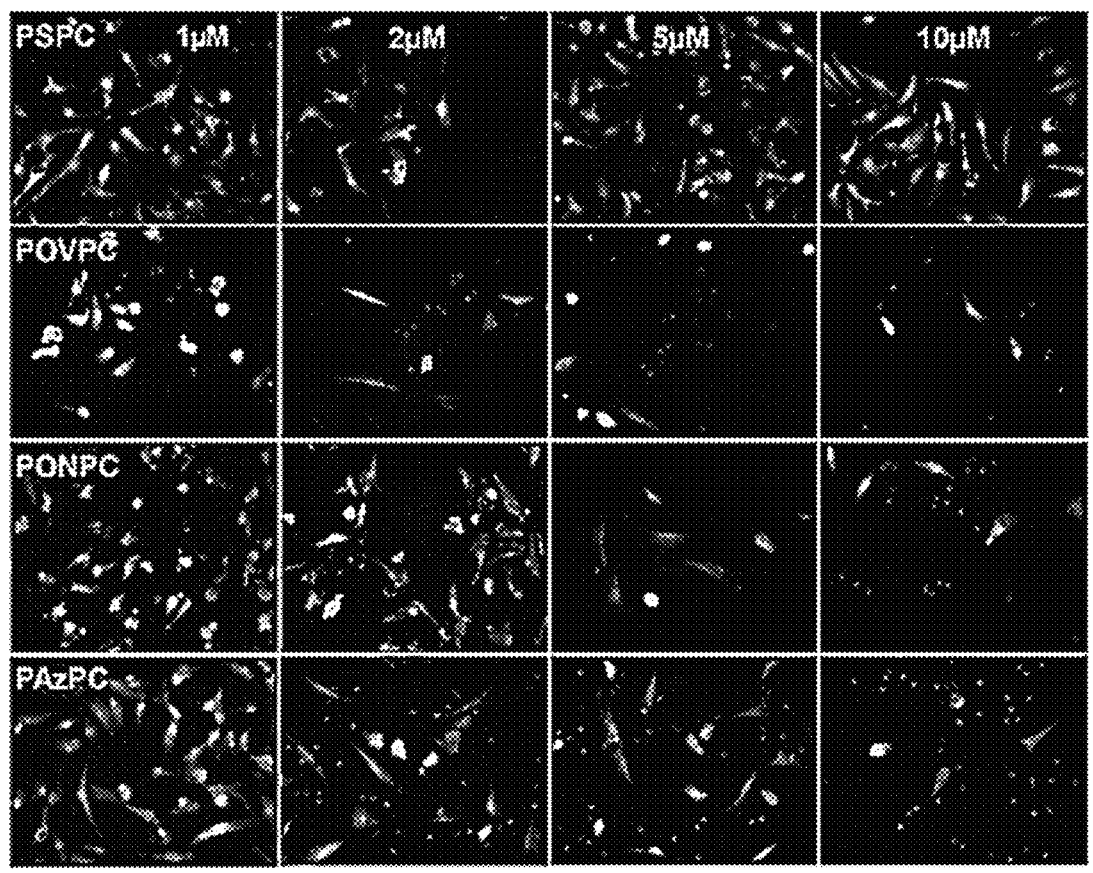
FIG. 5A-B shows cell viability of NNCM exposed to increasing concentrations of aldehyde and carboxylic acid based OxPL compared to cell viability after treatment with non-oxidized control PSPC. (A) Images of rat NNCM stained using the vital dyes, calcein-AM and ethidium homodimer-1, exposed to the indicated concentrations of the control phospholipid PSPC, and the OxPL POVPC, PAzPC and PONPC for 4 hrs at 37° C. (B) Cell viability measured as percent cell death after incubations with control PSPC and indicated OxPL (n=4) (*p<0.05, #p<0.01, vs PSPC at same concentration).
Figure 5B:
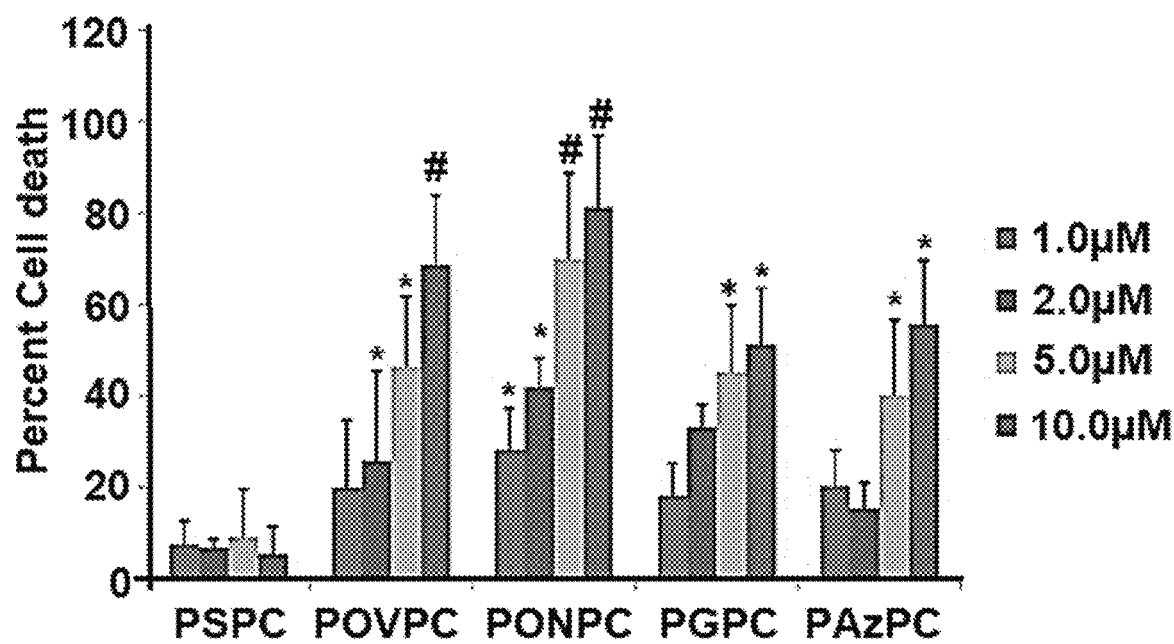

Experiments were performed to determine whether the specific OxPL species identified in the extracts of myocardium subjected to IR would have an effect on cell viability. Therefore, the identified OxPLs were incubated with NNCM in culture and their effect evaluated on cell viability, as compared to a non-oxidized phospholipid. (FIG. 5A). With increasing doses of OxPL, there was a progressive decrease in the number of calcein-AM stained live cells, and correspondingly, an increase in ethidium homodimer-1 staining dead cells. Each of the OxPL species resulted in significant cell death in a concentration-dependent pattern (FIG. 5B). PONPC was the most potent inducer of cardiomyocyte cell death when compared to control, resulting in 28.3±8.9%, 42.0±6.2%, 70.0±18.6%, and 81.2.6±15.1% for 1, 2, 5, and 10 µM respectively (p<0.001). POVPC was also a potent inducer of cell death with 68.6±14.8% at 10 µm (FIG. 5). The non-oxidized control PSPC treated NNCM showed non-significant increases in cell death at 1, 2, 5, and 10 µM, 7.6±5.1%, 9.1±10.5%, 10.5±1.6% and 5.5±1.6% respectively (vs. 7.0±1.1% control, p>0.05).

Figure 6A:
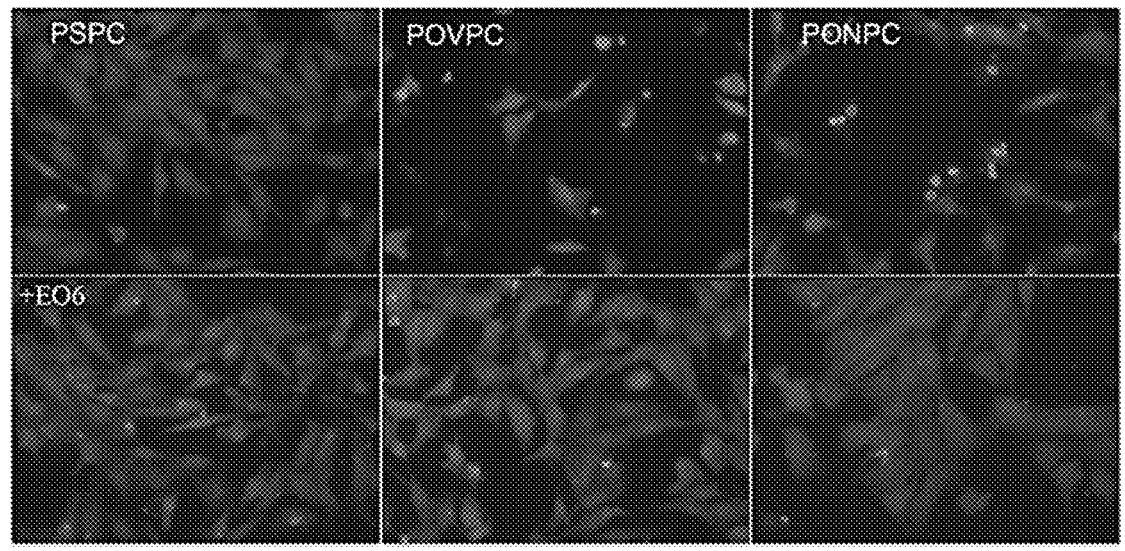
FIG. 6A-B shows attenuation of OxPL mediated cell death by E06. (A) Representative images of NNCM treated with POVPC and PONPC, and in presence of E06. NNCM stained using the vital dyes, calcein-AM and ethidium homodimer-1, co-treated with 5 µM of POVPC and PONPC and 10 µg/mL of OxLDL-specific E06 antibody for 2 hrs at 37° C. (B) There was significant inhibition of OxPL-induced cell death at 5 µM concentration. (n=4 separate cultures, each done in triplicate) (*p<0.05 when compared to PSPC, #p<0.05 when compare to POVPC and PONPC).
Figure 6B:
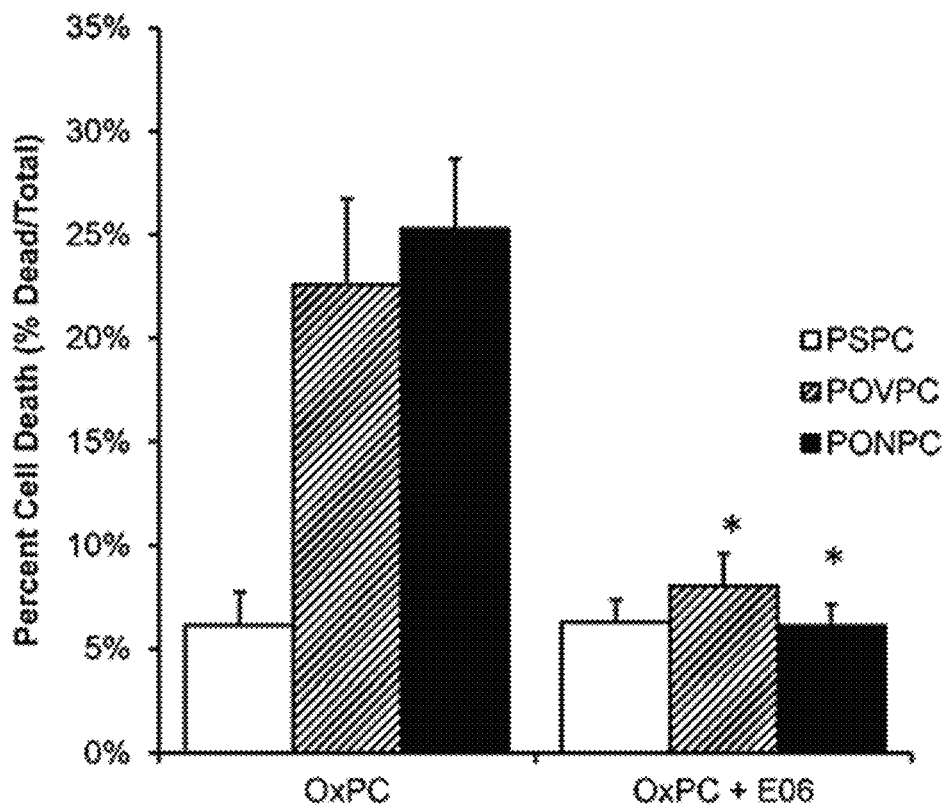

Neutralization of OxPL by E06 Attenuates Cell Death in vitro. To investigate whether inactivation of OxPL will prevent cell death, cardiomyocytes were exposed to 5 µM of PONPC and POVPC in the absence or presence of E06. In the presence of E06, OxPL mediated cardiomyocyte cell death was mitigated to near PSPC control treatment levels (FIG. 6A). 10 µg/mL of E06 inhibited POVPC induced cell death by 74.6% (22.6±4.14% vs 8.0±1.6%, p<0.05) and PONPC induced cell death by 74.7% (25.3±3.4% vs 6.4±1.0%, p<0.05) (FIG. 6B). The amount of cell death observed with PSPC treatment was unaffected by E06 co-treatment (6.2±1.6% without E06 vs 6.3±1.1% with E06).

Figure 7A:
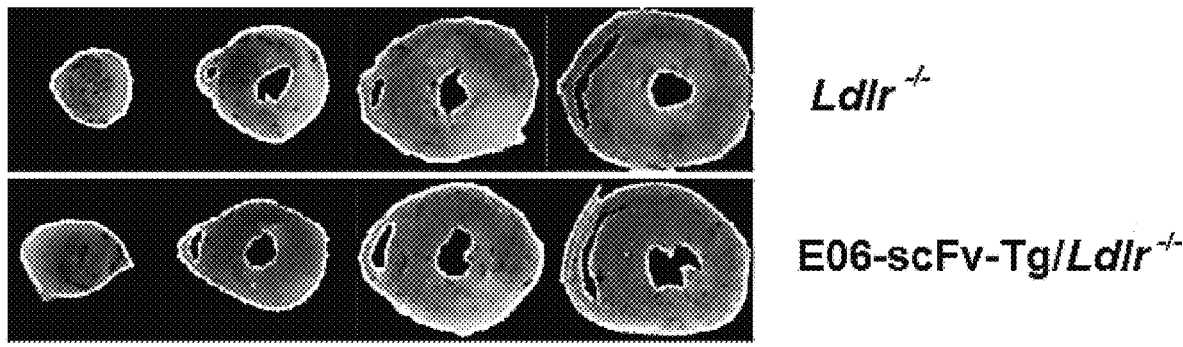
FIG. 7A-D shows mice expressing scFV-E06 have reduced infarct size following myocardial IR. (A) Representative myocardial TTC staining of $LDLR^{-/-}$ (n=15) and $scFvE06/LDLR^{-/-}$ (n=14) groups 7 days after 60 minutes of ischemia. White indicates infarct; red, viable myocardium; and non-blue, AAR. (B) There were no significant difference in AAR normalized by LV mass distal to the ligation for ischemia (AAR/LV). Compared to controls, E06-scFv/$Ldlr^{-/-}$ mice had 65.9% smaller IA/AAR (p=0.0023) (C) and 58.5% smaller IA/LV (p=0.0025)(D). TTC, 2,3,5-triphenyltetrazolium chloride; AAR, area at risk; LV, left ventricle; IA, infarct area.
Figure 7B:
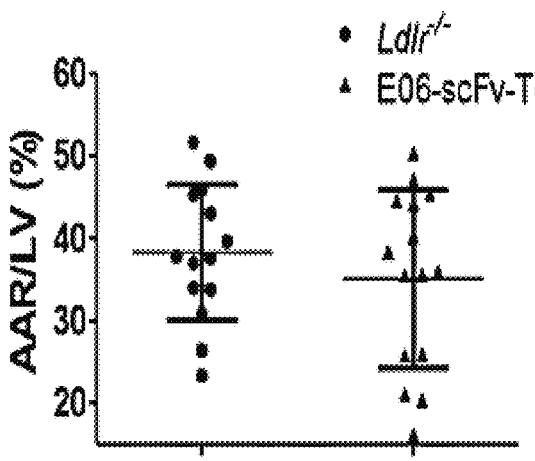
Figure 7C:
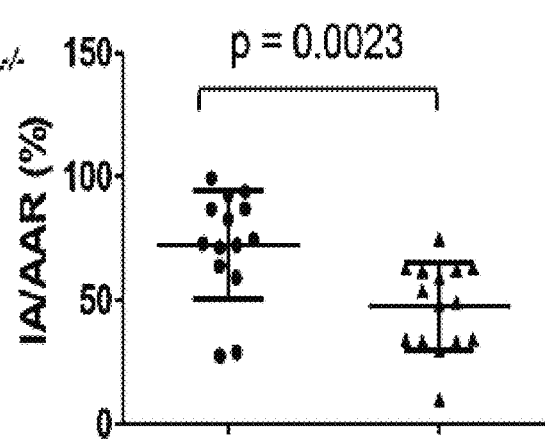
Figure 7D:
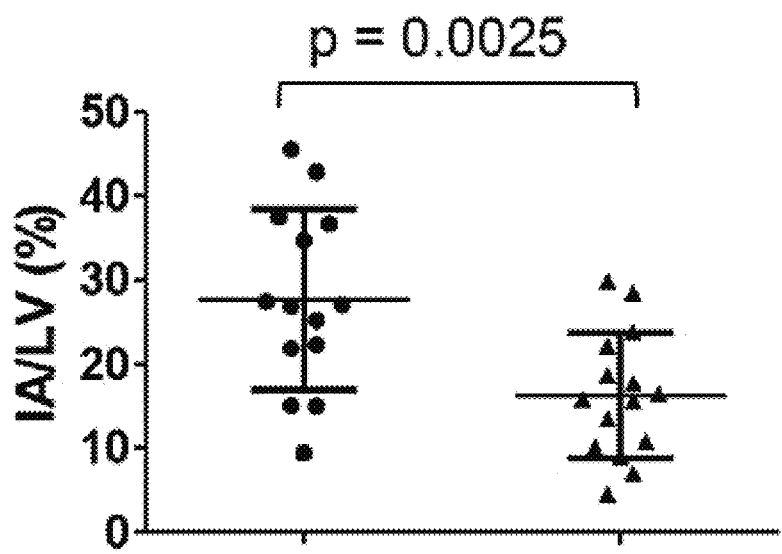

Neutralization of OxPL Reduces IR Infarct Size in vivo. Next, in order to evaluate the role of OxPL in vivo in mediating cell death under IR conditions, experiments were performed to evaluate if the in vivo neutralization of OxPL would attenuate IR infarct size in vivo. To accomplish this, transgenic mice were utilized that constitutively express a single-chain variable fragment of E06 (E06-scFv). The E06-scFv is under control of the apoE promoter and is expressed from hepatocytes and macrophages and is present in murine plasma at levels of 20-30 µg/mL. The E06-scFv-Tg mice were bred into the Ldlr$^{-/-}$ background. Fourteen E06-scFv-Tg/Ldlr$^{-/-}$ mice and fifteen Ldlr$^{-/-}$ animals were subjected to 60 minutes of left anterior descending artery (LAD) ischemia by suture ligation then reperfusion. Seven days after IR, myocardial infarct size was evaluated histologically (FIG. 7A). There was no significant difference in the area at risk (AAR) between the 2 groups, demonstrating that surgical ischemic injury was equivalent between groups (FIG. 7B). The ischemic area (IA) was then compared as a percentage of the AAR (IA/ARR) or as a percentage of the left ventricle LV (IA/LV) as measures of infarct size. Compared to the Ldlr$^{-/-}$ mice, the E06-scFv-Tg/Ldlr$^{-/-mice}$ had 65.9% smaller IA/AAR (47.7±17.6% vs 72.4±21.9%, p=0.023) (FIG. 7C) and a 58.8% smaller IA/LV ratio (16.3±7.5% vs 27.7±10.7%, p=0.025) (FIG. 7D).

A targeted approach was used to identify OxPL species generated following IR using mass spectrophotometry. While this approach offers precision in identifying specific OxPL using known standards, it does not rule out the contribution of OxPL species other than POVPC, PGPC, PAzPC, PONPC, KOdiAPC, and KDdiAPC or non-PC based oxidized phospholipids towards IR injury. However, the fact that E06 attenuates IR injury shows that OxPL, especially those examined in this study which are bound by E06, are clinically relevant oxidized phospholipids.

These studies identify an important role for OxPL as mediators of cell death during myocardial IR and that E06-scFv can attenuate IR infarct size. E06-scFv represent a novel potential therapeutic avenue to prevent the detrimental effects of IR injury and improve cardiac outcomes during acute myocardial infarction.

A number of embodiments have been described herein. Nevertheless, it will be understood that various modifications may be made without departing from the spirit and scope of this disclosure. Accordingly, other embodiments are within the scope of the following claims.

What is claimed is:

1. A method of reducing cardiomyocyte death associated with reperfusion-dependent oxidized phospholipid (OxPL) generation in a subject at risk thereof following a cardiac ischemic event, comprising
administering a therapeutically effective amount of an antibody or antibody fragment that specifically binds to a phosphocholine headgroup of an oxidized phospholipid to the subject, wherein the antibody or antibody fragment comprises: a variable heavy chain domain (VH) that includes complementarity determining regions (CDRs) comprising amino acid sequences that are at least 95% identical to each of SEQ ID NO:6, 7, and 8; and a variable light chain domain (VL) that includes CDRs comprising amino acid sequences that are at least 95% identical to each of SEQ ID NO:9 or 12, 10, and 11, wherein the antibody or antibody fragment is administered within 10 hours after the ischemic event.

2. The method of claim 1, wherein the antibody or antibody fragment is administered after the cardiac ischemic event and at the time of reperfusion.

3. The method of claim 1, wherein the antibody or antibody fragment is administered after the cardiac ischemic event and before reperfusion.

4. The method of claim 1, wherein the cardiac ischemic event is associated with a condition selected from the group consisting of cardiovascular ischemia, myocardial ischemia associated with myocardial infarction; and myocardial ischemia associated with congestive heart failure (CHF).

5. The method of claim 1, wherein the cardiac ischemic event is the result of an induced injury.

6. The method of claim 5, wherein the induced injury is the result of surgery, transplantation, accidental trauma, or application of a mechanical support device.

7. The method of claim 6, wherein the surgery is selected from the group consisting of heart surgery, kidney surgery, brain surgery, liver surgery, and bypass surgery.

8. The method of claim 1, wherein the antibody or antibody fragment lacks complement activation or inflammatory cell recruitment activity.

9. The method of claim 1, wherein the antibody or antibody fragment has the same or substantially the same binding affinity as an E06 antibody.

10. The method of claim 1, wherein the antibody or antibody fragment is administered continuously after the ischemic event.

11. The method of claim 1, wherein the administering results in a reduction in the severity of ischemic-reperfusion injury or inflammation arising from the ischemic event.

12. The method of claim 1, further comprising administering one or more additional agents useful to treat ischemia.

13. The method of claim 12, wherein the one or more additional agents are selected from the group consisting of a reperfusion agent, a free-radical scavenger agent, and a spin trap agent, a neuroprotective agent, an anticoagulant, an antiplatelet agent, nimodipine and naloxone.

14. The method of claim 1, further comprising administering one or more agents useful to treat a thrombotic disorder.

15. The method of claim 14, wherein the one or more agents useful to treat a thrombotic disorder are selected from the group consisting of an anticoagulant, heparin, a vitamin K antagonist, 4-hydroxycoumarin derivatives, warfarin, acenocoumarol, dicumarol, ethyl biscoumacetate, phenprocoumon, streptokinase, urokinase, tissue plasminogen activator (tPA), alteplase (recombinant tPA), reteplase, tenecteplase and argatroban.

16. The method of claim 1, wherein the antibody or antibody fragment is administered intravascularly or by an intracoronary route.

17. The method of claim 1, wherein the antibody fragment is a single chain variable fragment (scFv).

18. The method of claim 1, wherein: the VH domain comprises the CDR amino acid sequences set forth in SEQ ID NO:6, 7 and 8; and the VL domain comprises the CDR amino acid sequences set forth in SEQ ID NO:9, 10 and 11.

19. The method of claim 18, wherein: the VH comprises an amino acid sequence that is at least 95% identical to the VH amino acid sequence set forth in SEQ ID NO:2; and the VL comprises an amino acid sequence that is at least 95% identical to the VL amino acid sequence set forth in SEQ ID NO:2.

20. The method of claim 18, wherein: the VH comprises the VH amino acid set forth in SEQ ID NO:2; and the VL comprises the VL amino acid sequence set forth in SEQ ID NO:2.

21. The method of claim 1, wherein: the VH domain comprises the CDR amino acid sequences set forth in SEQ ID NO:6, 7 and 8; and the VL domain comprises the CDR amino acid sequences set forth in SEQ ID NO: 12, 10 and 11.

22. The method of claim 21, wherein: the VH comprises an amino acid sequence that is at least 95% identical to the VH amino acid sequence set forth in SEQ ID NO:4; and the VL comprises an amino acid sequence that is at least 95% identical to the VL amino acid sequence set forth in SEQ ID NO:4.

23. The method of claim 21, wherein: the VH comprises the VH amino acid set forth in SEQ ID NO:4; and the VL comprises the VL amino acid sequence set forth in SEQ ID NO:4.

* * * * *